(12) United States Patent
Bouck et al.

(10) Patent No.: US 6,919,309 B2
(45) Date of Patent: *Jul. 19, 2005

(54) METHODS AND COMPOSITIONS FOR INHIBITING ANGIOGENESIS

(75) Inventors: Noël P. Bouck, Occidental, CA (US); David W. Dawson, Los Angeles, CA (US); Paul R. Gillis, San Francisco, CA (US); Olga Volpert, Wilmette, IL (US); Susan E. Crawford, Burr Ridge, IL (US); Veronica M. Stellmach, Chicago, IL (US)

(73) Assignee: Northwestern University, Evanston, IL (US)

( * ) Notice: Subject to any disclaimer, the term of this patent is extended or adjusted under 35 U.S.C. 154(b) by 142 days.

This patent is subject to a terminal disclaimer.

(21) Appl. No.: 10/342,243

(22) Filed: Jan. 14, 2003

(65) Prior Publication Data

US 2003/0216286 A1 Nov. 20, 2003

Related U.S. Application Data

(60) Division of application No. 09/603,478, filed on Jun. 23, 2000, now Pat. No. 6,797,691, which is a continuation-in-part of application No. 09/511,683, filed on Feb. 23, 2000, now abandoned, which is a continuation-in-part of application No. 09/122,079, filed on Jul. 23, 1998, now Pat. No. 6,288,024, and a continuation-in-part of application No. PCT/US98/15228, filed on Jul. 23, 1998, which is a continuation-in-part of application No. 08/899,304, filed on Jul. 23, 1997, now abandoned.

(51) Int. Cl.$^7$ .............................................. A61K 38/16

(52) U.S. Cl. .............................. 514/2; 514/21; 424/574; 424/537; 424/571

(58) Field of Search ...................... 514/2, 21; 424/574, 424/537, 571

(56) References Cited

U.S. PATENT DOCUMENTS

| 4,160,452 | A | | 7/1979 | Theeuwes |
| 4,256,108 | A | | 3/1981 | Theeuwes |
| 4,265,874 | A | | 5/1981 | Bonsen |
| 4,996,159 | A | | 2/1991 | Glaser |
| 5,034,506 | A | | 7/1991 | Summerton et al. |
| 5,424,398 | A | | 6/1995 | Middeldorp et al. |
| 6,288,024 | B1 | * | 9/2001 | Bouck et al. ................... 514/2 |

FOREIGN PATENT DOCUMENTS

| WO | WO 93/24529 | 12/1993 |
| WO | WO 95/33480 | 12/1995 |

OTHER PUBLICATIONS

Adamis, et al., 1994, Am. J. Ophthalmol. 118:445.
Adamis, et al., 1996, Arch. Ophthalmol. 114:66.
Aiello, et al., 1994. N. Engl. J. Med. 331:1480.
Aiello, et al., 1995, Proc. Natl. Acad. Sci. U.S.A. 92:10457.
Altschul, et al., 1997, Nucleic Acids Res. 25:3389–3402.
Bain, et al., 1994, Gene Therapy 1:S68.
Barany, et al., 1987, Int. J. Peptide Protein Res. 30:705–739.
Becerra, et al., 1993, J. Biol. Chem. 268:23148–23156.
Becerra, et al., 1995, J. of Biol. Chemistry 270:25992–25999.
Becerra Chemistry and Biology of Serpins, Church, et al., Eds. (Plenum, New York, 1997), pp 223–237.
Berns and Giraud, 1995, Ann. N.Y. Acad. Sci. 772:95–104.
Bouck, et al., 1996, Adv. Cancer 69:135.
Connolly et al., 1988, Microvas. Res. 36:275.
Dipaolo, et al., 1995, Exp. Cell Res. 220:178–185.
Federoff, et al., 1992, Proc. Natl. Acad. Sci. USA 89:1636–1640.
Fink, et al., 1996, Ann. Rev. Neurosci. 19:265–287.
Folkman and Klagsbrun, 1987, Science 235:442–447.
Folkman and Shing, 1989, J. Biol. Chem. 267(16):10931–10934.
Folkman, et al., 1995, Molecular Basis of Cancer 206–232.
Folkman, 1986, J. Cancer Res. 46:467–473.
Folkman, 1989, J. Nat. Cancer Inst. 82:4–6.
Gasparini, 1996, Eur. J. Cancer 32A(14):2379–2385.
Goldberg, et al., 1988, Science 242:1214.
Gulledge and Dewhirst, 1996, Anticancer Res. 16:741.
Hanahan and Folkman, 1996, Cell 86:353.
Hayasaka, et al., 1998, Life Sci. 63:1089.
Kaminska and Niederkorn, 1993, Investig. Ophthalmol. Vis. Sci. 34:222.
O'Reilly, et al., 1994, Cell 79:315–328.
O'Reilly, et al., 1997, Cell 88:277–285.
Ogata, et al., 1997, Curr. Eye Res. 16:9.
Pierce, et al., 1996, Arch. Ophthalmol. 114:1219.
Pignolo, et al., 1993, J. Biol. Chem. 268:8949.
Polverini, et al., 1991, Methods in Enzymology 198:440–450.
Polverini, et al., 1991 Methods Enzymol 194:440.
Provis, et al., 1997, Exp. Eye Res. 65:555.

(Continued)

*Primary Examiner*—Jean C. Witz
(74) *Attorney, Agent, or Firm*—Morgan, Lewis & Bockius LLP

(57) ABSTRACT

The present invention provides a method of inhibiting angiogenesis within a tissue by providing exogenous PEDF to cells associated with the tissue. The presence of exogenous PEDF inhibits angiogenesis within the tissue, in part by interfering with the ability of vascular endothelia to expand within the tissue. The invention also provides a method for determining the severity of a tumor by assaying for the presence of PEDF within the tumor. The invention further provides a method of inhibiting endothelial cell migration, a method of stimulating the growth of hair in a mammal, a method for inhibiting the growth of a tumor, a method of inducing differentiation of a neuroblastoma cell, a method of slowing the growth of a neuroblastoma cell, and method of treating ischemic retinopathy in a mammal. To facilitate the inventive methods, the present invention provides pharmaceutical compositions including sources of PEDF.

5 Claims, 24 Drawing Sheets

OTHER PUBLICATIONS

Smith, et al., 1995, Invest. Ophthalmol. Vis. Sci. 35:101.
Steele, et al., 1993, Proc. Natl. Acad. Sci. USA 90(4):1526–1530.
Sugita, et al., 1997, J. Neurosci. Res. 49:710–718.
Tanawaki, et al., 1995, J. Neurochem. 64:2509–2517.
Teicher, et al., 1994, Int. J. Cancer 57:920–925.
Tombran–Tink, et al., 1991, Exp. Eye Res. 53:411–414.
Tombran–Tink, et al., 1995, J. Neurosci., 15:4992–5003.
Vinores, et al., 1998, J. Neuroimmunol. 89:43.
Weidner, 1991, New Eng. Med. 324(1):1–8.
Wu and Beccerra, 1996, Investig. Ophthalmol. Vis. Sci. 37:1984–1993.
Xu et al., 1991, Cancer Res. 51:4481–4485.

* cited by examiner

MQALVLLLCIGALLGHSSCQNPASPPEEGSPDPD
STGALVEEEDPFFKVPVNKLAAAVSNFGYDLYRV
RSSMSPTTNVLLSPLSVATALSALSLGADERTES
IIHRALYYDLISSPDIHGTYKELLDTVTAPQKNL
KSASRIVFEKKLRIKSSFVAPLEKSYGTRPRVLT
GNPRLDLQEINNWVQAQMKGKLARSTKEIPDEIS
ILLLGVAHFKGQWVTKFDSRKTSLEDFYLDEERT
VRVPMMSDPKAVLRYGLDSDLSCKIAQLPLTGSM
SIIFFLPLKVTQNLTLIEESLTSEFIHDIDRELK
TVQAVLTVPKLKLSYEGEVTKSLQEMKLQSLFDS
PDFSKITGKPIKLTQVEHRAGFEWNEDGAGTTPS
PGLQPAHLTFPLDYHLNQPFIFVLRDTDTGALLF
IGKILDPRGP

```
GGACGCTGGA TTAGAAGGCA GCAAAAAAG ATCTGTGCTG GCTGGAGCCC CCTCAGTGTG CAGGCTTAGA
GGGACTAGGC TGGGTGTGGA GCTGCAGCGT ATCCACAGGC CCCAGGATGC AGGCCCTGGT GCTACTCCTC
TGCATTGGAG CCCTCCTCGG GCACAGCAGC TGCCAGAACC CTGCCAGCCC CCCGGAGGAG GGCTCCCCAG
ACCCCGACAG CACAGGGGCG CTGGTGGAGG AGGAGGATCC TTTCTTCAAA GTCCCCGTGA ACAAGCTGGC
AGCGGCTGTC TCCAACTTCG GCTATGACCT GTACCGGGTG CGATCCAGCA TGAGCCCCAC GACCAACGTG
CTCCTGTCTC CTCTCAGTGT GGCCACGGCC CTCTCGGCCC TCTCGCTGGG AGCGGACGAG CGAACAGAAT
CCATCATTCA CCGGGCTCTC TACTATGACT TGATCAGCAG CCCAGACATC CATGTACCT ATAAGGAGCT
CCTTGACACG GTCACTGCCC CCCAGAAGAA CCTCAAGAGT GCCTCCCGGA TCGTCTTTGA GAAGAAGCTR
CGCATAAAAT CCAGCTTTGT GGCACCTCTG GAAAAGTCAT GCCCAGAGTC CTGACGGGCA
CGCATAAAAT CCAGCTTTGT GGCACCTCTG GAAAAGTCAT GCCCAGAGTC CTGACGGGCA
ACCCTCGCTT GGACCTGCAA GAGATCAACA ACTGGGTGCA GGCGCAGATG AAAGGGAAGC TCGCCAGGTC
CACAAAGGAA ATTCCCGATG AGATCAGCAT TCTCCTTCTC GGTGTGGCGC ACTTCAAGGG GCAGTGGTA
ACAAAGTTTG ACTCCAGAAA GACTTCCCTC GAGGATTTCT ACTTGGATGA AGAGAGACC GTGAGGGTCC
CCATGATGTC GGACCCTAAG GCTGTTTTAC GCTATGGCTT GGATTCAGAT CTCAGCTGCA AGATTGCCCA
GCTGCCCTTG ACCGGAAGCA TGAGTATCAT CTTCTTCCTG CCCCTGAAAG TGACCCAGAA TTTTGACCTTG
ATAGAGGAGA GCCTCACCTC CGAGTTCATT CATGACATAG ACCGAGAACT GAAGACCGTG CAGGCGGTCC
TCACTGTCCC CAAGCTGAGG CTGAGTTACG AAGGCGAAGT CACCAAGTCC CTGCAGGAGA TGAAGCTGCA
ATCCTTGTTT GATTCACCAG ACTTTAGCAA GATCACAGGC AAACCCATCA AGCTGACTCA GGTGGAACAC
CGGGCTGGCT TTGAGTGGAA CGAGGATGGG GCGGGAACCA CCCCCAGCCC AGGGCTGCAG CCTGCCCACC
TCACCTTCCC GCTGGACTAT CACCCTTAACC AGCCTTTCAT CTTCGTACTG AGGACACAG ACACAGGGGC
CCTTCTCTTC GCTGAGGACA TTCTGGACCC CAGGGGCCCC CAGGGGCCCC TAATATCCCA GTTAATATATT CCAATACCCT
AGAAGAAAAC CCGAGGGACA GCAGATTCCA CAGGACACGA AGGCTGCCAG TGTAAGGTTT CAATGCATAC
AATAAAGAG CTTTATCCCT
```

FIG.8A
FIG.8C
FIG.8B

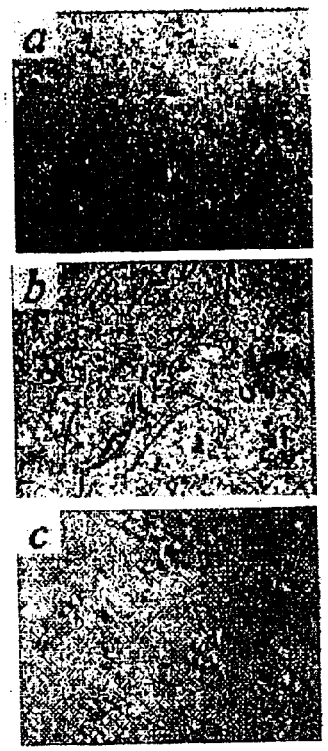
FIG.10A
FIG.10B
FIG.10C
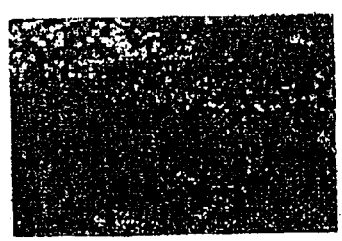 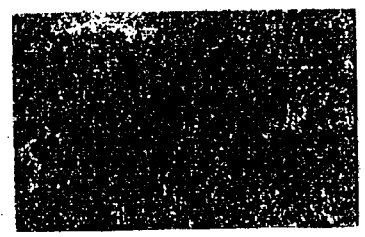
FIG.11A    FIG.11B
 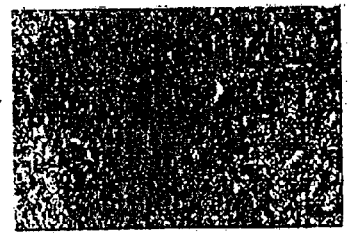 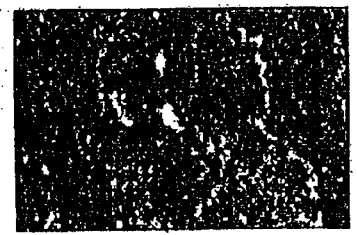
FIG.11C    FIG.11D    FIG.11E

FIG. 13A

| Sample | bFGF (0.15nM) | anti-PEDF (20 micrograms per milliliter) | anti-TGF-beta (50 micrograms per milliliter) | Positive Corneas/Total Implanted |
|---|---|---|---|---|
| 1. PBS | - | - | - | 0/2 |
| 2. PBS | + | - | - | 8/8 |
| 3. PBS | - | + | - | 5/5 |
| 4. PBS | - | - | + | 0/2 |
| 5. PEDF peptide | - | - | - | 0/2 |
| 6. PEDF peptide | - | + | - | 1/4* |
| 7. rPEDF | - | - | - | 0/2 |
| 8. rPEDF | + | - | - | 0/3 |
| 9. pPEDF | - | - | - | 0/3 |
| 10. pPEDF | + | - | - | 0/3 |
| BEFORE PEDF REMOVAL | | | | |
| 11. Vitreous | - | - | - | 0/4 |
| 12. Vitreous | + | - | - | 0/4 |
| 13. Vitreous | - | - | + | 0/3 |
| 14. Vitreous | + | - | + | 0/3 |
| 15. Cornea extract | - | - | - | 0/3 |
| 16. Cornea extract | + | - | - | 1/4 |
| AFTER PEDF REMOVAL | | | | |
| 17. Vitreous | - | - | - | 6/6 |
| 18. Cornea extract | - | - | - | 4/4 |
| 19. Cornea extract | + | - | - | 3/3 |

*One cornea gave a mild response with a few sprouting vessels that did not reach the pellet.

FIG.13B-1 bFGF
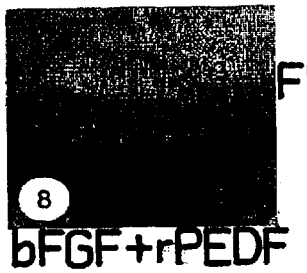
FIG.13B-5 bFGF+rPEDF
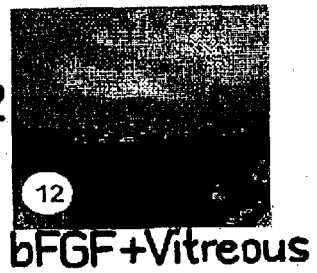
FIG.13B-2 bFGF+Vitreous
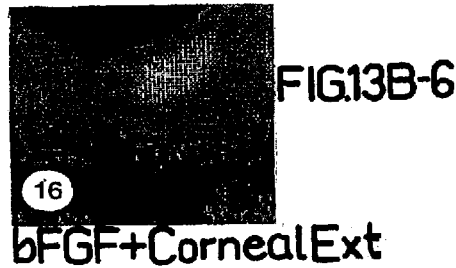
FIG.13B-6 bFGF+CornealExt
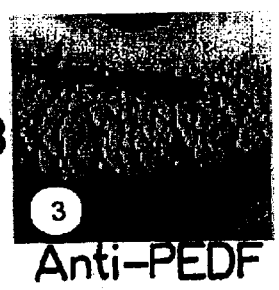
FIG.13B-3 Anti-PEDF
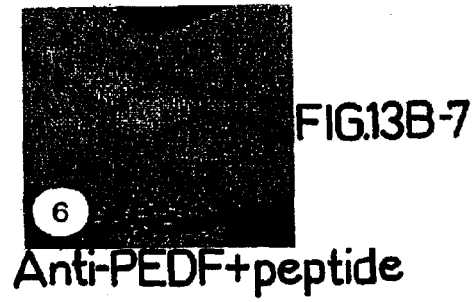
FIG.13B-7 Anti-PEDF+peptide
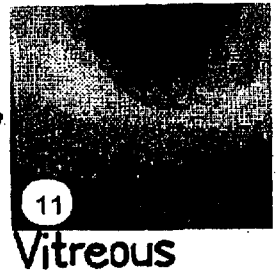
FIG.13B-4 Vitreous
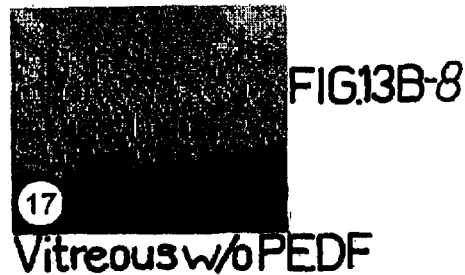
FIG.13B-8 Vitreous w/o PEDF

METHODS AND COMPOSITIONS FOR INHIBITING ANGIOGENESIS

CROSS-REFERENCE TO RELATED APPLICATIONS

This application is a division of Ser. No. 09/603,478 filed Jun. 23, 2000 now U.S. Pat. No. 6,797,691 which is a continuation-in-part of Ser. No. 09/511,683 filed Feb. 23, 2000 now abandoned which is a continuation-in-part of Ser. No. 09/122,079 Jul. 23, 1998 now U.S. Pat. No. 6,288,024 and is a continuation-in-part of PCT/US98/15228 filed Jul. 23, 1998 which is a continuation-in-part of Ser. No. 08/899,304 filed Jul. 23, 1997 now abandoned.

STATEMENT REGARDING FEDERALLY SPONSORED RESEARCH OR DEVELOPMENT

This invention was supported in part by funds obtained from the U.S. Government (National Institutes of Health Grant Numbers CA52750 and CA64239), and the U.S. Government may therefore have certain rights in the invention.

BACKGROUND OF THE INVENTION

Angiogenesis is the fundamental process by which new blood vessels are formed. The process involves the migration of vascular endothelial cells into tissue followed by the condensation of such endothelial cells into vessels. Angiogenesis may be induced by an exogenous angiogenic agent or may be the result of a natural condition. The process is essential to a variety of normal body activities such as reproduction, development and wound repair. Although the process is not completely understood, it involves a complex interplay of molecules that stimulate and molecules that inhibit the growth and migration of endothelial cells, the primary cells of the capillary blood vessels. Under normal conditions, these molecules appear to maintain the microvasculature in a quiescent state (i.e., without capillary growth) for prolonged periods which can last for several years or even decades. The turnover time for an endothelial cell is about one thousand days. However, under appropriate conditions (e.g., during wound repair), these same cells can undergo rapid proliferation and turnover within a much shorter period, and a turnover rate of five days is typical under these circumstances. (Folkman and Shing, 1989, J. Biol. Chem. 267(16):10931–10934; Folkman and Klagsbrun, 1987, Science 235:442–447).

Although angiogenesis is a highly regulated process under normal conditions, many diseases (characterized as "angiogenic diseases") are driven by persistent unregulated angiogenesis. In such disease states, unregulated angiogenesis can either cause a particular disease directly or exacerbate an existing pathological condition. For example, ocular neovascularization has been implicated as the most common cause of blindness and underlies the pathology of approximately twenty diseases of the eye. In certain previously existing conditions such as arthritis, newly formed capillary blood vessels invade the joints and destroy cartilage. In diabetes, new capillaries formed in the retina invade the vitreous humor and bleed, causing blindness.

Both the growth and metastasis of solid tumors are also angiogenesis-dependent (Folkman, 1986, J. Cancer Res. 46:467–473; Folkman, 1989, J. Nat. Cancer Inst. 82:4–6; Folkman et al. 1995, "Tumor Angiogenesis," Chapter 10, pp. 206–32, in The Molecular Basis of Cancer, Mendelsohn et al., eds. (W. B. Saunders). It has been shown, for example, that tumors which enlarge to greater than about 2 mm in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner 1991, New Eng. J. Med. 324(1):1–8). When used as drugs in tumor-bearing animals, natural inhibitors of angiogenesis can prevent the growth of small tumors (O'Reilly et al., 1994, Cell 79:315–328). Indeed, in some protocols, the application of such inhibitors leads to tumor regression and dormancy even after cessation of treatment (O'Reilly et al., 1997, Cell 88:277–285). Moreover, supplying inhibitors of angiogenesis to certain tumors can potentiate their response to other therapeutic regimens (e.g., chemotherapy) (see, e.g., Teischer et al., 1994, Int. J. Cancer 57:920–925).

Although several angiogenesis inhibitors are currently under development for use in treating angiogenic diseases (Gasparini, 1996, Eur. J. Cancer 32A(14):2379–2385), there are disadvantages associated with these proposed inhibitory compounds. For example, suramin is a potent angiogenesis inhibitor, but, at doses required to reach antitumor activity, causes severe systemic toxicity in humans. Other compounds, such as retinoids, interferons and antiestrogens appear safe for human use but have only a weak anti-angiogenic effect. Still other compounds may be difficult or costly to make. In addition, the simultaneous administration of several different inhibitors of angiogenesis may be needed for truly effective treatment.

There remains, therefore, a long felt need for the development of new methods and compositions for inhibiting angiogenesis. The present invention satisfies these needs.

BRIEF SUMMARY OF THE INVENTION

The invention includes a method of inhibiting angiogenesis within a tissue. The method comprises providing exogenous PEDF to endothelial cells associated with the tissue under conditions sufficient for the PEDF to inhibit angiogenesis within the tissue.

In several embodiments, the tissue is eye tissue, is skin tissue, a tumor, a tissue within a joint, bone marrow, nasal epithelium, prostate or ovarian or endometrial tissue.

In one aspect, the method further comprises supplying another antiangiogenic factor to the cells in conjunction with PEDF.

In yet another aspect, the PEDF is provided to the cells by exposing a composition comprising PEDF polypeptide to the cells.

In a further aspect, the PEDF is provided to the cells by transferring to the cells a vector, the vector comprising an isolated nucleic acid encoding PEDF, whereby the PEDF is expressed in and secreted from the cells.

In one embodiment, the isolated nucleic encoding PEDF comprises SEQ ID NO:2, and in another embodiment, the isolated nucleic acid encoding PEDF encodes a biologically active fragment of PEDF. Preferably, the biologically active fragment of PEDF is contained within the amino acid sequence of SEQ ID NO:1. More preferably, the biologically active fragment of PEDF comprises from amino acid 44 and amino acid 121 of SEQ ID NO:1; and even more preferably, the biologically active fragment of PEDF comprises amino acids 44–77 of SEQ ID NO:1.

In other preferred embodiments, the PEDF comprises SEQ ID NO:1 or a biologically active fragment of SEQ ID NO:1, wherein, in other preferred embodiments, the biologically active fragment of PEDF comprises from amino acids 44 to amino acids 121 of SEQ ID NO:1, or preferably comprising amino acids 44–77 of SEQ ID NO:1.

In one embodiment, the PEDF is provided to the endothelial cells by transfecting into a population of other cells a vector, the vector comprising an isolated nucleic acid encoding PEDF, whereby the PEDF is expressed in and secreted from the other cells, and transferring the population of the other cells so transfected to a site where PEDF so secreted is cable of contacting the endothelial cells.

In one embodiment, the isolated nucleic acid is SEQ ID NO:2, or in another embodiment, the isolated nucleic acid is a biologically active fragment of PEDF. Preferably, the biologically active fragment of PEDF is encoded by a fragment of SEQ ID NO:2.

In another embodiment, transfection of the isolated nucleic acid into the population of other cells results in expression of PEDF from non-integrated or stably integrated DNA in the other cells.

In other aspects of the invention, the PEDF is supplied to the cells via the systemic circulation, or via topical administration.

The invention also includes a method of inhibiting endothelial cell migration. The method comprises providing exogenous PEDF to the cells under conditions sufficient for the PEDF to inhibit endothelial cell migration.

The invention further includes a method of stimulating the growth of hair in a mammal. This method comprises providing exogenous PEDF to cells associated with the skin of the mammal under conditions sufficient for the PEDF to stimulate the growth of hair in the mammal.

Also included is a method for inhibiting the growth of a tumor. This method comprises providing exogenous PEDF to endothelial cells associated with the tumor under conditions sufficient for the PEDF to inhibit the migration of the endothelial cells within and to the tumor such that the growth of the tumor is inhibited.

In one embodiment, the method further comprises supplying another antiangiogenic factor to the cells in conjunction with PEDF.

In another embodiment, the PEDF is provided to the cells by exposing a composition comprising PEDF polypeptide to the cells.

In yet another embodiment, the PEDF is provided to the cells by transferring to the cells a vector, the vector comprising an isolated nucleic acid encoding PEDF, whereby the PEDF is expressed in and secreted from the cells.

In another embodiment, the PEDF is provided to the endothelial cells by transfecting into a population of other cells a vector, the vector comprising an isolated nucleic acid encoding PEDF, whereby the PEDF is expressed in and secreted from the other cells, and transferring the population of the other cells so transfected to a site where PEDF so secreted is capable of contacting the endothelial cells.

In several embodiments, the PEDF is supplied to the cells via the systemic circulation or via topical administration.

The invention further includes a pharmacological composition comprising a source of PEDF and a suitable diluent. In one aspect, the source of PEDF is PEDF polypeptide. In another aspect, the source of PEDF is a vector comprising an isolated nucleic acid encoding PEDF.

Further included in the invention is a method of determining the severity of a tumor by assaying for the presence of PEDF within the tumor, wherein the absence of PEDF within the tumor indicates an advanced state and the presence of PEDF within the tumor indicates an early state of the tumor.

In addition, the invention includes a method of inducing differentiation of a neuroblastoma cell. The method comprises administering PEDF to the cell, thereby inducing differentiation of the cell.

The invention also includes a method of slowing the growth of a neuroblastoma cell. The method comprises administering PEDF to the cell, thereby slowing the growth of the cell.

The invention further includes a method of treating ischemic retinopathy in a mammal. The method comprises providing exogenous PEDF to endothelial cells associated with the eye of the mammal under conditions sufficient for the PEDF to inhibit angiogenesis in the eye, thereby treating the ischemic retinopathy.

Also included is a method of inhibiting angiogenesis within a tissue in a mammal. The method comprises providing exogenous PEDF systemically to the mammal, under conditions sufficient for the PEDF to inhibit angiogenesis within the tissue.

In one embodiment, the tissue is selected from the group consisting of eye tissue, skin tissue, a tumor, a tissue within a joint, bone marrow, nasal epithelium, prostate, ovarian and endometrial tissue. Preferably, the tissue is eye tissue.

Also preferably, the mammal is selected from the group consisting of a mammal that has ischemic retinopathy, a mammal that is at risk for developing ischemic retinopathy, a mammal that has macular degeneration and a mammal that is at risk for developing macular degeneration.

In another embodiment, the method further comprises supplying another antiangiogenic factor to the cells in conjunction with PEDF.

Also included is a method of upregulating the expression of PEDF in a cell in a tissue. This method comprises inducing hyperoxia in the tissue, thereby upregulating the expression of PEDF in the cell.

The invention further includes a method of treating macular degeneration in a mammal. The method comprises providing exogenous PEDF to endothelial cells associated with the eye of the mammal under conditions sufficient for said PEDF to inhibit angiogenesis in the eye, thereby treating the macular degeneration.

Also included is a method of treating a benign neoplasia in a mammal, the method comprising administering PEDF to the mammal, thereby treating the benign neoplasia. Preferably, the benign neoplasia is a nasal polyp, more preferably, in a human having cystic fibrosis. Also preferably, the benign neoplasia is in the prostate gland.

The invention further includes a method of inhibiting angiogenesis within a tissue. The method comprising providing exogenous PEDF to endothelial cells associated with the tissue in conjunction with at least one other treatment selected from the group consisting of radiation, chemotherapy, the use of at least one biological response modifier, laser treatment, under conditions sufficient for the PEDF to inhibit angiogenesis within the tissue.

BRIEF DESCRIPTION OF THE DRAWINGS

FIG. 2, comprising FIG. 2A depicts data concerning WI-38 cells from human epithelium. FIG. 2B depicts data concerning human foreskin fibroblasts. FIG. 2C depicts data concerning human vascular smooth muscle cells. FIG. 2D depicts data concerning human neutrophils.

FIG. 6, comprising FIGS. 6A and 6B, is the amino acid sequence of full length PEDF (SEQ ID NO:1) and the nucleic acid sequence which encodes full length PEDF (SEQ ID NO:2). Due to naturally occurring polymorphisms, at the amino acid level, amino acid residues 97 and 98 may be EQ or DE, and at the DNA level, the corresponding nucleotides encoding these amino acids may therefore be GAG CAG or GAC GAG.

FIG. 7, comprising

FIG. 8, comprising FIGS. 8A, 8B and 8C, is a series of images of photomicrographs of sections of skin obtained from animals treated with PEDF, wherein hair follicles are depicted. Human neuroblastoma tumors growing subcutaneously in nude mice were injected at 2–3 sites/tumor for four consecutive days with 2 µg of purified PEDF. On the fifth day, hair was noticed growing over the treated tumors. Histological sections (see PEDF treated, FIGS. 8B and 8C) exhibited a three-fold increased density of hair follicles compared with skin overlying tumors treated with vehicle only (PBS-treated, FIG. 8A). Similar increases in hair follicle density have been seen in the absence of tumors following injection of purified PEDF.

FIG. 9, comprising

FIG. 10, comprising FIGS. 10A–10C, is a series of photomicrographs of cultured human neuroblastoma cells that have been treated in vitro with buffer (control, FIG. 10A), with PEDF (FIG. 10B), or with PEDF in the presence of neutralizing anti-PEDF antibodies (FIG. 10C). A high frequency of neurite outgrowth indicating differentiation is seen only in FIG. 10B.

FIG. 11, comprising FIGS. 11A–11E, is a series of photomicrographs taken of human neuroblastoma tumors growing in nude mice that have been injected with the vehicle phosphate buffered saline (PBS; FIGS. 11A and 11B) or that have been injected with human PEDF (FIGS. 11C, 11D and 11E). The neuroblastomas were fixed and stained for neurofilament protein, an indicator of differentiation. Dramatically increased staining and therefore differentiation can be seen in the treated tumors. In FIG. 11C, differentiation is clearly present along the needle track (clear rectangle in upper center) where the PEDF was injected.

FIG. 12, comprising FIG. 12A: PEDF (0.1 µg/ml) purified from WERI-Rb-27R (Xu, et al., 1991, Cancer Res. 51:4881) medium was tested alone or in combination with antibody against recombinant PEDF (anti-EPC-1; 20 µg/ml) or against PEDF peptide (anti-PEDF; 1 µg/ml) for its ability to inhibit the migration of bovine capillary endothelial cells toward antiangiogenic bFGF (10 ng/ml). PEDF antipeptide antibody (anti-PEDF) was raised in rabbits against a peptide containing PEDF amino acids 327 to 343, conjugated to Keyhole-limpet hemocyanin, and affinity-purified on a peptide column. Polyclonal antisera against bacterial recombinant PEDF/EPC-1 (anti-EPC-1) is described in DiPaolo, et al. (1995, Exp. Cell Res. 220:178) and the antiangiogenic protein angiostatin is described in O'Reilly, et al. (1994, Cell 79:315). Purchased reagents included neutralizing anti-VEGF (Genzyme, Cambridge, Mass.), pan antibodies to TGFβ, and all angiogenic inducers (R & D Systems, Minneapolis, Minn.) except lysophosphatidic acid (Sigma Chemical Co. St. Louis, Mo.). All protein and antibodies were extensively dialyzed against PBS before use in biological assays. Migration assays were performed in quadruplicate for each sample with bovine adrenal capillary endothelial cells or human dermal microvascular endothelial cells (Clonetics, San Diego, Calif.) as described (Polverini, et al., 1991, Methods Enzymol. 194:440). To combine multiple experiments, background migration (Bkgd) was first subtracted toward vehicle (0.1% bovine serum albumin) and then the data were normalized by setting maximum migration toward inducer alone to 100%. All experiments were repeated two to five times. Statistics were performed on raw data before normalization with the Student's t test. Standard errors were converted to percentages. FIG. 12B: Increasing concentrations of angiostatin (O) or recombinant PEDF (●) were tested as in FIG. 12A. Human PEDF cDNA was engineered by polymerase chain reaction to encode a COOH-terminal hexahistidine tag, cloned into pCEP4 (Invitrogen, Carlsbad, Calif.), and transfected into human embryonic kidney cells. Recombinant PEDF was purified from the conditioned media with the Xpress Protein Purification System (Invitrogen, Carlsbad, Calif.). FIG. 12C: Human vitreous fluid diluted as indicated and a human corneal stromal extract (used at 10 µg of protein per milliliter) were assayed in the presence of the inducer VEGF (0.1 ng/ml) or anti-PEDF (1 µg/ml) (or in the presence of both VEGF and anti-PEDF). Human vitreous fluid was withdrawn from three cadaveric eyes (refrigerated within 1.4 to 4.5 hours of death) obtained from individuals without ocular disease. Fluid was frozen until used. Fresh vitreous fluid was obtained from bovine and mouse eyes. For preparation of stromal extract, corneas were freed of associated epithelium and as much of the endothelium as possible, washed extensively in ice-cold phosphate-buffered saline (PBS, pH 7.4), and minced into small fragments that were incubated for 24 hours in PBS containing 0.5 mM phenylmethanesulfonyl fluoride. The extract was filter sterilized, stored at −80° C., and tested in migration assays at a final concentration of 10 μg of protein per milliliter. Bars indicate standard error of mean (SEM) of five separate experiments (FIG. 12A. In the case of FIGS. 12B and 12C, data from one representative experiment are shown with standard errors.

FIG. 13, comprising FIGS. 13A and 13B, is a table and a series of images of photomicrographs depicting inhibition of neovascularization by purified PEDF and by PEDF present naturally in normal human vitreous and cornea. FIG. 13A: Recombinant (rPEDF) or purified (pPEDF) PEDF (8 nM), PEDF peptide 327 to 343 (299 μg/ml), undiluted vitreous fluid, or corneal extract (used at 200 μg of protein per milliliter) was incorporated with vehicle (PBS) and the indicated additions into Hydron pellets that were implanted into the avascular rat cornea. Vigorous ingrowth of vessels from the limbus toward the pellet by 7 days was scored as a positive response (Polverini, et al, 1991, Methods Enzymol 198:440). Where noted, anti-PEDF linked to protein A beads was used to remove PEDF from vitreous fluid and corneal extract. FIG. 13B, comprising FIGS. 13B-1 through 13B-8: Representative photos of corneal responses from FIG. 13A shown at X13 magnification. PEDF antipeptide antibody (anti-PEDF) was raised in rabbits against a peptide containing pEDF amino acids 327–343, conjugated to Keyhole-limpet hemocyanin, and affinity-purified on a peptide column. Polyclonal antisera against bacterial recombinant PEDF/EPC-1 (anti-EPC-1) is described in DePaolo, et al. (1995, Exp. Cell Res. 220:178) and the antiangiogenic protein angiostatin is descried in O'Reilly, et al. (194, Cell 79:315). Purchased reagents included neutralizing anti-VEGF (Genzyme Cambridge, Mass.), pan antibodies to TGFβ, and all angiogenic inducers (R&D Systems, Minneapolis, Minn.) except lysophosphatidic acid (Sigma). All proteins and antibodies were extensively dialyzed against PBS before use in biological assays. FIG. 13B-1 corresponds to sample 2 of FIG. 13A; FIG. 13B-2 corresponds to sample 12 of FIG. 13A, FIG. 13B-3 corresponds to sample 3 of FIG. 13A; FIG. 13B-4 corresponds to sample 11 of FIG. 13A; FIG. 13B-5 corresponds to sample 8 of FIG. 13A; FIG. 13B-6 corresponds to sample 16 of FIG. 13A; FIG. 13B-7 corresponds to sample 6 of FIG. 13A; FIG. 13B-8 corresponds to sample 17 of FIG. 13A.

FIG. 14, comprising

FIG. 15, comprising FIG. 15A: Immunoblot analysis of PEDF present in media from cultures of three Rb-negative cells lines (WERI-Rb-27, Y79, and WERI-Rb-1; all from American Type Culture Collection, Rockville, Md.) and from one Rb-positive line (WERI-Rb-27R) (Xu, et al., 1991, Cancer Res. 51:4481). Cells were maintained in normoxia (N; 21% $O_2$), Hypoxia (H; 05% $O_2$), or $CoCl_2$ (Co; 100 μM), and serum-free media were collected over a 48-hour period from equivalent numbers of cells. The blot containing 5 μg of protein per lane was probed with anti-PEDF and developed with ECL (Amersham, Arlington Heights, Ill.). FIG. 15B: Northern blot of total cellular RNA (10 μg per lane) isolated from WERI-Rb-27 cells after exposure to hypoxia for 24 to 48 hours. Blots were probed with 1.5-kb full-length PEDF cDNA or an 819-base pair β-actin probe to control for loading. Numbers indicate ratio of PEDF to β-actin mRNA levels as determined by densitometry. FIG. 15C: Medium (used at 2 μg of total protein per milliliter) from normoxic or hypoxic WERI-Rb-1 cells was tested for ability to induce the migration of human dermal microvascular endothelial cells. Migration assays were performed in quadruplicate for each sample with bovine adrenal capillary endothelial cells or human dermal microvascular endothelial cells (Clonetics, San Diego, Calif.) as described (Polverini, et al., 1991, Methods Enzymol 194:440). To combine multiple experiments, background migration (Bkgd) was first subtracted toward vehicle (0.1% bovine serum albumin) and then normalized data by setting maximum migration toward inducer alone to 100%. All experiments were repeated two to five times. Statistics were performed on raw data before normalization with the Student's t test. Standard errors were converted to percentages. Assays contained medium alone or medium plus neutralizing anti-PEDF (1 μg/ml) or anti-VEGF (20 μg/ml). VEGF-induced migration was completely abrogated by anti-VEGF and unaffected by anti-PEDF. PEDF antipeptide antibody (anti-PEDF) was raised in rabbits against a peptide containing PEDF amino acids 327 to 343, conjugated to Keyhole-limpet hemocyanin, and affinity-purified on a peptide column. VEGF-induced migration was completely abrogated by anti-VEGF and unaffected by anti-PEDF. Neither antibody affected migration when tested alone. One hundred percent equaled 67 cells migrated in 10 high-power fields.

FIG. 16, comprising

DETAILED DESCRIPTION OF THE INVENTION

Figure 1:
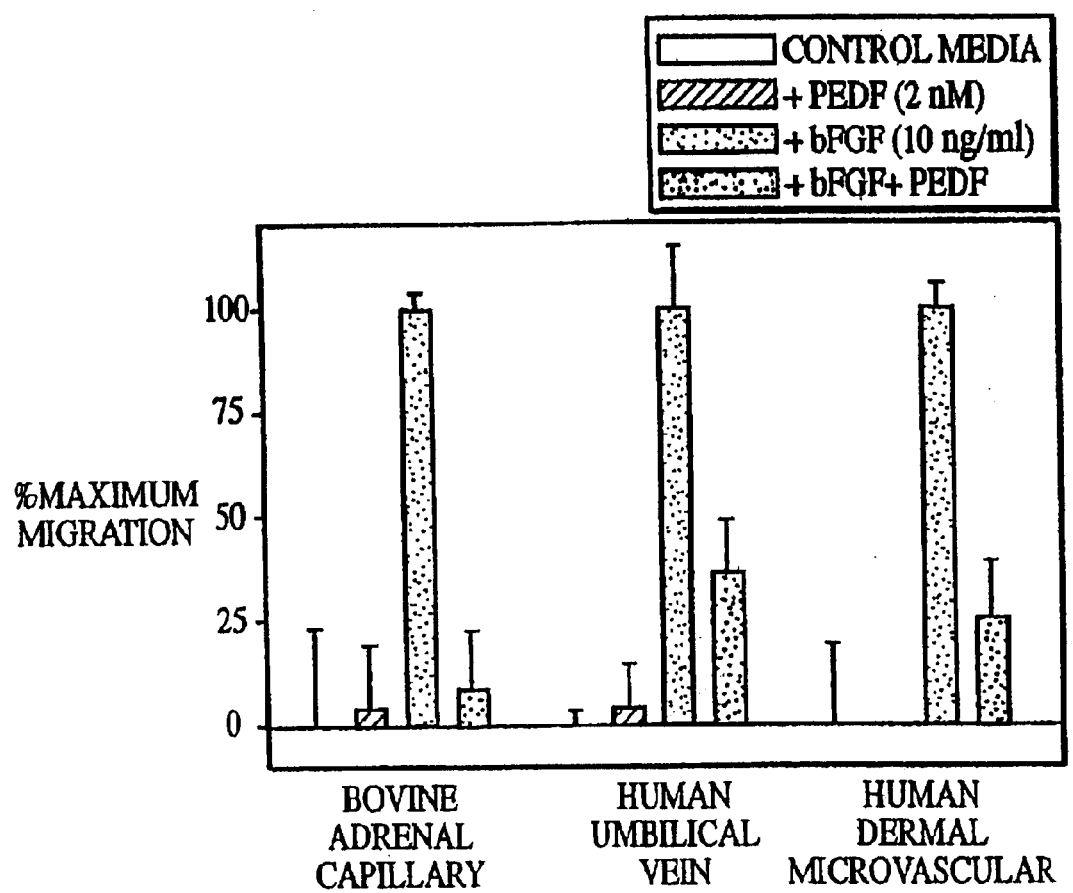
FIG. 1 graphically illustrates the ability of PEDF to inhibit the migration of endothelial cells derived from large and small vessels and human and bovine species.
Figure 2A:
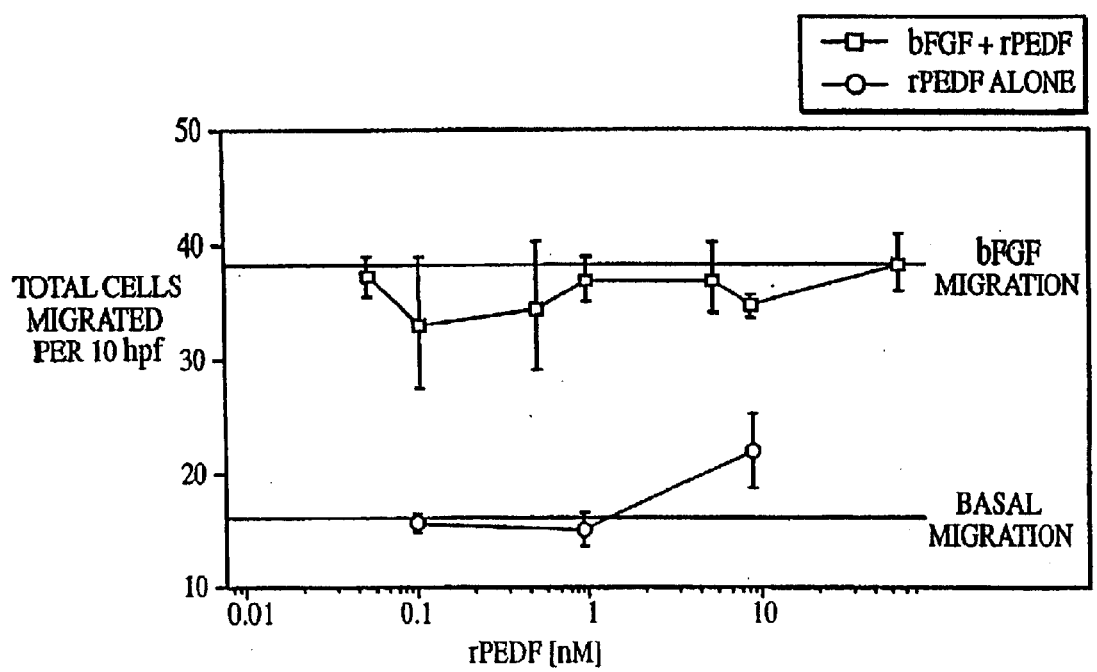
FIGS. 2A–2D, illustrates the specificity of PEDF for vascular endothelia by graphically representing the inability of various doses of PEDF to inhibit the migration of cells other than vascular endothelial cells.
Figure 2B:
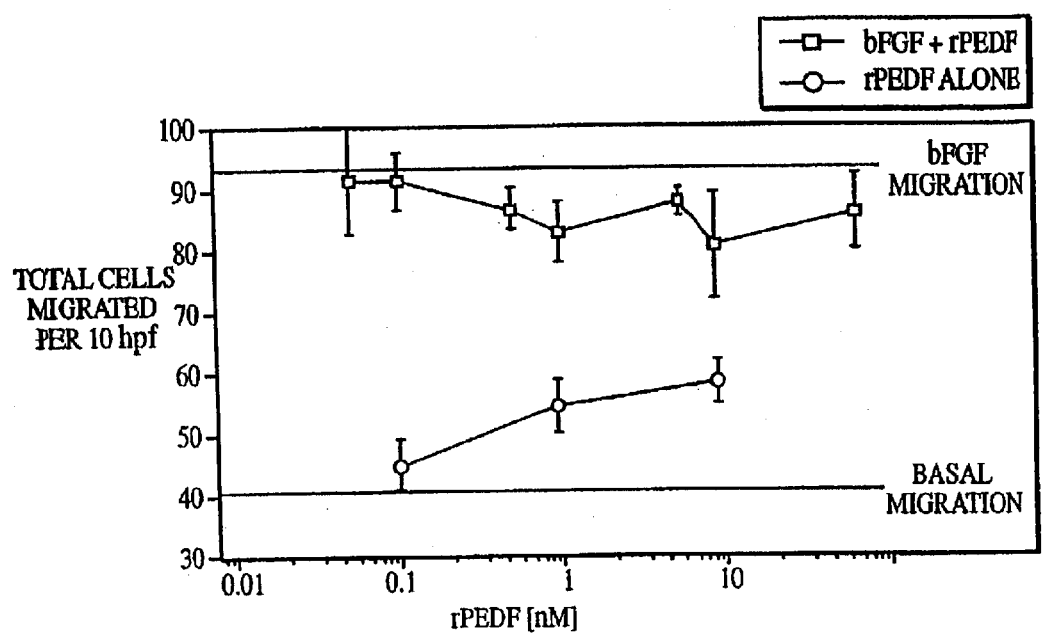
Figure 2C:
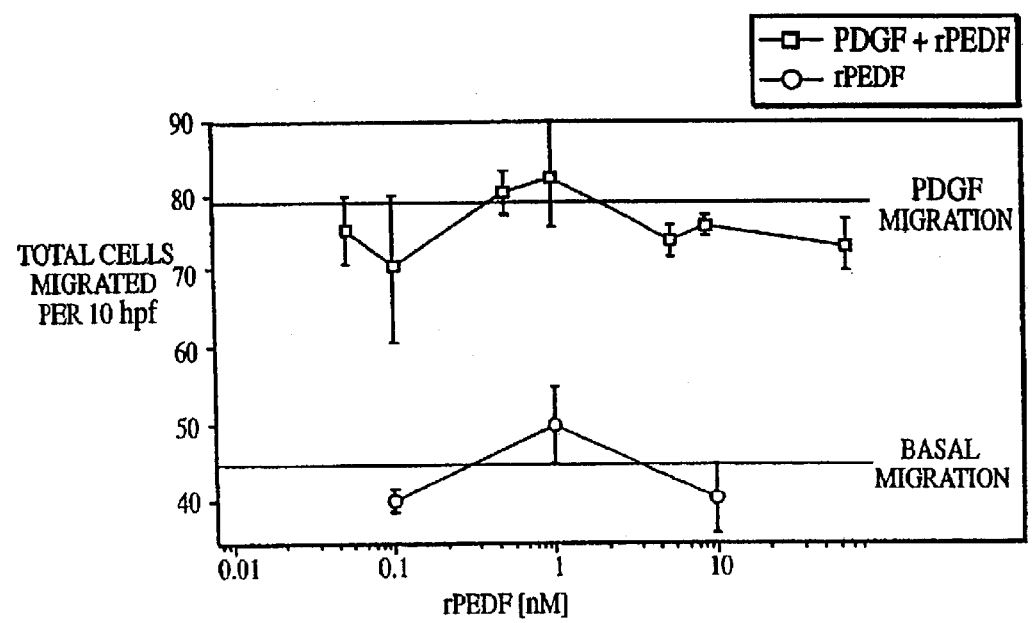
Figure 2D:
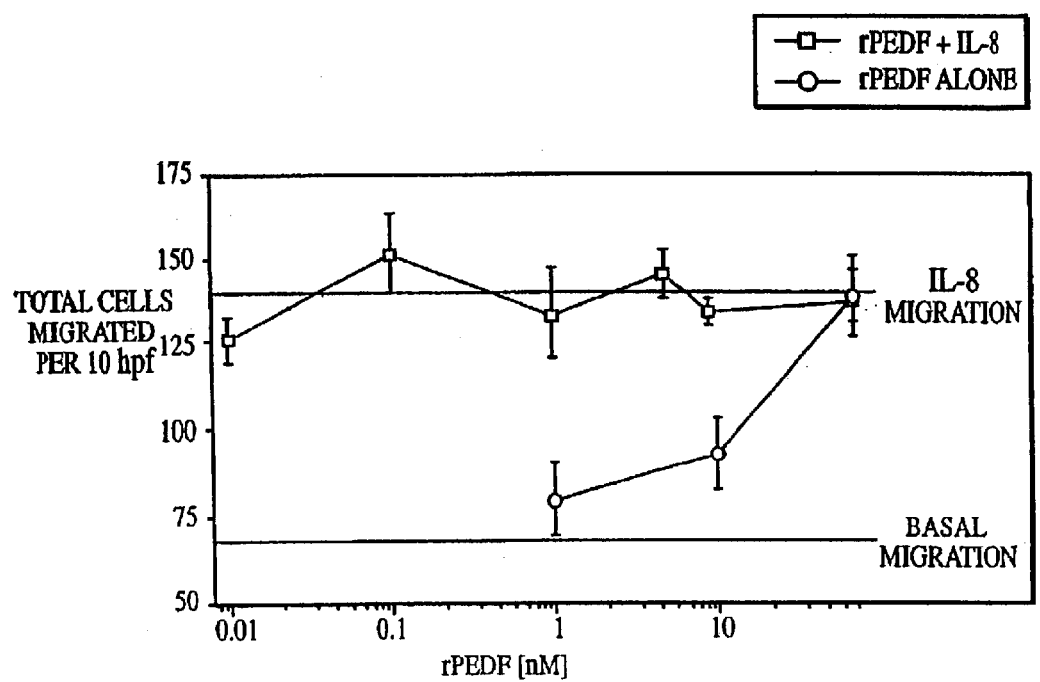

The invention encompasses the use of full length pigment epithelium derived growth factor (PEDF; Steele et al., 1993, Proc. Natl. Acad. Sci. USA 90(4):1526–1530) and any antiangiogenic derivative of PEDF for inhibiting angiogenesis. The invention also encompasses the use of nucleic acid encoding full length PEDF and any antiangiogenic derivative of PEDF for inhibiting angiogenesis.

Within the context of the inventive method, PEDF is a protein having potent antiangiogenic properties, and it includes any antiangiogenic derivative of PEDF, such as those described herein. One form of PEDF polypeptide (full length PEDF) is set forth in FIG. 6A (SEQ ID NO:1);

however, the invention is not limited to the use of this exemplary sequence. Indeed, other PEDF sequences are known in the art (see, e.g., published international patent applications WO 95/33480 and WO 93/24529). Further, it is well known that genetic sequences can vary between different species and individuals. This natural scope of allelic variation is included within the scope of the present invention. Additionally and alternatively, a PEDF polypeptide can include one or more point mutations from the exemplary sequence or another naturally occurring PEDF polypeptide. Thus, a PEDF polypeptide is typically at least about 75% homologous to all or a portion of SEQ ID NO:1 and preferably is at least about 80% homologous to all or a portion of SEQ ID NO:1 (e.g., at least about 85% homologous to SEQ ID NO:1); more preferably the PEDF polypeptide is at least about 90% homologous to all or a portion of SEQ ID NO:1 (such as at least about 95% homologous to all or a portion of SEQ ID NO:1), and most preferably the PEDF polypeptide is at least about 97% homologous to all or a portion of SEQ ID NO:1. Indeed, the PEDF polypeptide can also include other domains, such as epitope tags and His tags (e.g., the protein can be a fusion protein).

Within the context of the present invention, a PEDF polypeptide can be or comprise insertion, deletion, or substitution mutants of a known PEDF sequence or derivative thereof. Preferably, any substitution is conservative in that it minimally disrupts the biochemical properties of the PEDF polypeptide. Thus, where mutations are introduced to substitute amino acid residues, positively-charged residues (H, K, and R) preferably are substituted with positively-charged residues; negatively-charged residues (D and E) preferably are substituted with negatively-charged residues; neutral polar residues (C, G, N, Q, S, T, and Y) preferably are substituted with neutral polar residues; and neutral non-polar residues (A, F, I, L, M, P, V, and W) preferably are substituted with neutral non-polar residues. Moreover, the PEDF polypeptide can be an active fragment of a known PEDF protein or fragment thereof. Indeed, it has been found that truncated fragments derived from SEQ ID NO:1 are active PEDF polypeptides. For example, it is believed that residues 1 through 20 of SEQ ID NO: 1 are cleaved during secretion and thus are dispensable for PEDF activity. Moreover, other active PEDF natural and synthetic polypeptides comprise sequences derived from residues 21 through 382 of SEQ ID NO:1, such as residues 44 through 157 of SEQ ID NO:1 (e.g., residues 44–121, and 44–77 SEQ ID NO:1). Of course, while insertion, deletion, or substitution mutations can affect glycosylation of the protein, a PEDF polypeptide need not be glycosylated to possess the requisite antiangiogenic properties for use in the inventive method. For example, see the data presented in FIG. 7 wherein the active 34 amino acid fragment of PEDF is not glycosylated.

The invention should further be construed to include the use of a PEDF polypeptide which may contain one or more D-isomer forms of the amino acids of PEDF. Production of a retro-inverso D-amino acid PEDF peptide where the peptide is made with the same amino acids as disclosed, but at least one amino acid, and perhaps all amino acids are D-amino acids is a simple matter once armed with the present invention. When all of the amino acids in the peptide are D-amino acids, and the N- and C- terminals of the molecule are reversed, the result is a molecule having the same structural groups being at the same positions as in the L-amino acid form of the molecule. However, the molecule is more stable to proteolytic degradation and is therefore useful in many of the applications recited herein.

The method of the invention should also be construed to include the use of PEDF in the form of nucleic acid encoding biologically active PEDF, as exemplified in FIG. 6B (SEQ ID NO:2) or any fragment thereof having PEDF biological activity, as defined herein. Thus the invention should be construed to include the use of nucleic acid which encodes the aforementioned fragments of PEDF and any derivatives thereof and nucleic acid which is substantially homologous to SEQ ID NO:2 or a fragment thereof encoding biologically active PEDF.

By the term "biologically active PEDF" as used herein is meant any PEDF polypeptide, fragment or derivative which is capable of inhibiting angiogenesis in any of the assays presented in the experimental details/examples section contained herein.

A biologically active fragment of PEDF is exemplified herein in the examples section as being a 34 amino acid fragment of PEDF (34 mer). The procedures for the isolation and characterization of this fragment are provided in detail herein in view of the state of skill in the art. Thus, it is an easy matter, following the directions provided herein, to identify biologically active fragments of PEDF useful in the present invention and the invention therefore must be construed to include any and all such fragments and any modifications and derivatives thereof, as disclosed herein. In addition, the invention should be construed to include any and all nucleic acids which encode biologically active fragments of PEDF as that term is defined herein. The term "PEDF" used in the claims appended hereto, should be construed to include all forms of biologically active PEDF as defined herein.

By the term "exogenous" as used herein to refer to PEDF, the term should be construed to include any and all PEDF which is not naturally expressed in a cell. For example, "exogenous PEDF" should be construed to include PEDF expressed from a nucleic acid which has been introduced into a cell using recombinant technology, PEDF which is added to a cell and any and all combinations thereof. Therefore, the term should not be construed to be limited solely to the addition of PEDF to a cell per se, but should be expanded to include the expression of PEDF in a cell when the PEDF is expressed from a nucleic acid which has been introduced into the cell.

PEDF polypeptides inhibit angiogenesis, in part, by attenuating the migration and survival of activated endothelial cells, thus reducing the ability of endothelia to expand within the tissue. Thus, the invention provides a method of inhibiting endothelial cell migration by providing exogenous PEDF to such cells. Aside from attenuating angiogenesis, the method is useful for treating disorders associated with stimulation of endothelial cell migration such as intestinal adhesions, Crohn's disease, atherosclerosis, scleroderma and hypertrophic scars (e.g., keloids).

In accordance with the inventive method, PEDF is provided to endothelial cells associated with the tissue of interest. Such cells can be cells comprising the tissue of interest, exogenous cells introduced into the tissue, or neighboring cells not within the tissue. Thus, for example, the cells can be cells of the tissue, and PEDF is provided to them in situ such that the PEDF contacts the cells. Alternatively, the cells can be cells introduced into the tissue, in which case the PEDF can be transferred to the cells before they are so introduced into the tissue (e.g., in vitro), as well as being transferred in situ after introduction into the tissue.

When PEDF is introduced into cells which are then transferred to the mammal, the invention should not be construed as being limited by the manner in which PEDF is introduced into the cells. Nor should the invention be construed to be limited to the manner in which the cells are introduced to the mammal. As described in more detail below, methods of introducing DNA into cells are well known as are methods of delivering such cells to a tissue in a mammal.

The tissue with which the endothelial cells are associated is any tissue in which it is desired to inhibit the migration or expansion of endothelia, (e.g., for inhibiting angiogenesis). In one application, the tissue can be eye tissue, in which case the presence of exogenous PEDF will inhibit novel angiogenesis associated with a variety of disorders of the eye. For example, the inventive method is useful for treating eye injury, hypoxia, infection, surgery, laser surgery, diabetes, retinoblastoma, macular degeneration, ischemic retinopathy, or other diseases or disorders of the eye. In this respect, the method is useful for preventing blindness or retarding loss of vision associated with a variety of eye diseases. The vast majority of diabetic patients eventually suffer vision impairment due to overgrowth of vessels in the retina in response to ischemia caused by the disease. Similarly, premature infants exposed to high levels of oxygen develop retinopathy as a result of retinal vein occlusion or other vascular or ischemic abnormalities. As described herein, ischemic-induced retinopathies may be prevented and or treated with by systemic or local administration of PEDF. In the case of laser surgery, with respect to the eye, PEDF may be used to prevent the re-growth of vessels after treatment. Lasers are used to destroy excessive vessels, but they also create a wound in the retina that induces some angiogenesis. Systemic or local treatment with PEDF should serve to prevent such re-growth.

By the term "retinopathy" as used herein, is meant the abnormal development of blood vessels within or around the retina that may or may not enter the vitreous. Injury, disease, ischemic events, laser or other iatrogenic treatments may induce retinopathy.

In another application, the tissue is skin tissue, in which case the presence of exogenous PEDF prevents neovascularization associated with several skin diseases. For example, the inventive method is useful for treating diseases and disorders such as psoriasis, scleroderma, tumors of the skin, neovascularization as a consequence of infection (e.g., cat scratch disease, bacterial ulceration, etc.) or other skin disorders. Where PEDF is provided to the skin, it can be provided to the surface of the skin or to skin tissue beneath the skin's surface, or even systemically. Furthermore, transfer of PEDF to skin of a mammal can also stimulate the growth of hair in the skin. Without being bound by any particular theory, it is believed that PEDF affects hair growth by mediating angiogenesis within the hair follicle and/or by influencing differentiation of nearby neuronal tissue.

In other embodiments, the tissue is a tumor (e.g., a benign or cancerous growth), in which case the inventive method will inhibit the growth of blood vessels within and to the tumor, and in some cases, induce tumor cells to differentiate and thus divide slowly. Inhibiting the growth of blood vessels within tumors prevents sufficient nutrients and oxygen from being supplied to the tumor to support growth beyond a given size. Thus, the inventive method can prevent the nucleation of tumors from cancerous cells already present due to genetic predisposition (e.g., BRCA-1 mutation carriers, Li Fraumeni patients with p53 mutations, etc.) or the presence of external carcinogens (e.g., tobacco, alcohol, industrial solvents, etc.). Aside from preventing tumorigenesis, the inventive method can retard the growth of existing tumors, thus rendering them more easily contained and excised and may cause them to regress. This application is highly advantageous for treating tumors that are difficult to operate on (e.g., brain or prostate tumors). In addition, the method is useful for treatment of childhood tumors, including, but not limited to, neuroblastoma. Moreover, minimizing the number of blood vessels within existing tumors lessens the probability that the tumor will metastasize. In treating tumors, the method can be used alone or in conjunction with other treatments, to control the growth of tumors. Indeed, employing the inventive method can potentiate the response of some tumors to other therapies. For example, the inventive method optionally can be employed as a pretreatment for (e.g., for about a week in advance of), and continued during, a chemotherapeutic or radiation regimen. The method of the invention may also be used in conjunction with the use of biological response modifiers, such as for example, interferon, or other anti-angiogenic agents, and also is useful in conjunction with the use of agents which induce the production of anti-angiogenic agents in vivo. Further, the method of the invention may be used in conjunction with agents which promote the differentiation of cells, particularly, but not limited to agents which promote the differentiation of brain tumor cells.

Where the inventive method is applied to other tissues, the prevention of neovascularization effectively treats a host of disorders. Thus, for example, the inventive method can be used as part of a treatment for disorders of blood vessels (e.g., hemangiomas and capillary proliferation within atherosclerotic plaques), muscle diseases (e.g., myocardial angiogenesis or angiogenesis within smooth muscles), joints (e.g., arthritis, hemophiliac joints, etc.), and other disorders associated with angiogenesis (e.g., Osler-Webber Syndrome, plaque neovascularization, telangiectasia, angiofibroma, wound granularization, etc.). In addition, the invention is useful for treatment of nasal polyps, especially in cystic fibrosis patients, leukemia which stems from bone marrow cell abnormal growth, and prostate cancer. The invention can be construed in general to be useful for treatment of benign neoplasias.

Aside from treating disorders and symptoms associated with neovascularization, the inhibition of angiogenesis can be used to modulate or prevent the occurrence of normal physiological conditions associated with neovascularization. with the inventive method, the presence of PEDF within the ovaries or endometrium Thus, for example, the inventive method can be used as a birth control. In accordance can attenuate neovascularization associated with ovulation, implantation of an embryo, placenta formation, etc.

The inventive method is also useful as a means of preventing the occurrence of a disease or disorder associated with angiogenesis, i.e., the methods are useful as prophylactic methods for the prevention of disease in patients at risk for the disease. For example, and without limitation, PEDF may be used to prevent the onset of diabetic retinopathy in a patient having diabetes, to prevent the onset of cancer in persons known to be at risk for certain cancers, and the like. Thus, the methods of the invention should not be construed as being limited to treatment of overt disease, but rather, should be construed as being useful for the prevention of disease in patients who are at risk.

The invention should also be construed to include treatment of precancerous lesions, for example, but without limitation, nasal polyps, particularly in patients having cystic fibrosis. Nasal polyps in these patients are angiogenic, and further, the cerebral spinal fluid of cystic fibrosis patients contains an excess of the angiogenic factor VEGF.

Alleviation of these conditions, especially in cystic fibrosis patients, wherein the alleviation comprises administration of PEDF is therefore included in the present invention.

Within the context of the inventive method, PEDF can be supplied alone or in conjunction with other known antiangiogenic factors. For example, PEDF can be used in conjunction with antibodies and peptides that block integrin engagement, proteins and small molecules that inhibit metalloproteinases (e.g., marmistat), agents that block phosphorylation cascades within endothelial cells (e.g., herbamycin), dominant negative receptors for known inducers of angiogenesis, antibodies against inducers of angiogenesis or other compounds that block their activity (e.g., suramin), or other compounds (e.g., retinoids, IL-4, interferons, etc.) acting by other means. Indeed, as such factors modulate angiogenesis by different mechanisms, employing PEDF in combination with other antiangiogenic agents can potentiate a more potent (and potentially synergistic) inhibition of angiogenesis within the desired tissue. PEDF can be used with one or more other antiangiogenic factors. Preferably, at least two antiangiogenic factors may be used in conjunction with PEDF.

As discussed herein, PEDF is a proteinatious factor. Thus, in one protocol, the method involves providing PEDF by supplying a PEDF polypeptide to the cells (e.g., within a suitable composition). Any suitable method can be employed to obtain a PEDF polypeptide for use in the present invention. Many suitable PEDF polypeptides can be purified from tissues which naturally produce PEDF or from media conditioned by a variety of PEDF-producing cells (e.g., retinoblastoma cell line WER127). For example, it is known that PEDF is produced by all types of muscle, megakaryocytes of the spleen, fibroblasts, kidney tubules, cerebellar Purkinje cells, piliosebaceous glands of hair follicles, and retinal cells. A particularly good source of naturally occurring PEDF is vitreous and aqueous humors extracted from the eye. One protocol for purifying PEDF from protein extracts of these (or other sources) is by concentration/dialysis using a 30 kDa ultrafiltration membrane followed by protein precipitation in a range of about 65% to about 95% ammonium sulfate, followed by a lentil lectin sepharose column at 0.5 M methyl-α-D-mannopytanoside, followed by gradient/isocratic elution at 0.5 M NaCl from a PHARMACIA HiTrap heparin column. Other protocols for purifying PEDF polypeptides are known in the art (see, e.g., published international patent applications WO 95/33480 and WO 93/24529). The native PEDF polypeptide represented by SEQ ID NO:1 is identified via SDS-PAGE as a protein of about 45 to 50 kDa. Other PEDF polypeptides can be synthesized using standard direct peptide synthesizing techniques (e.g., as summarized in Bodanszky, 1984, Principles of Peptide Synthesis (Springer-Verlag, Heidelberg), such as via solid-phase synthesis (see, e.g., Merrifield, 1963, J. Am. Chem. Soc. 85:2149–2154; Barany et al., 1987, Int. J. Peptide Protein Res. 30:705–739; and U.S. Pat. No. 5,424,398). Of course, as genes for PEDF polypeptides are known (see, e.g., published international patent applications WO 95/33480 and WO 93/24529); see also GenBank accession no. U29953), or can be deduced from the polypeptide sequences discussed herein, a PEDF polypeptide can be produced by standard recombinant DNA methods.

In other protocols, PEDF polypeptide can be provided to the tissue of interest by transferring an expression vector including a nucleic acid encoding PEDF to cells associated with the tissue of interest. The cells produce and secrete the PEDF polypeptide such that it is suitably provided to endothelial cells within the tissue to inhibit their migration and, thus, to attenuate angiogenesis within the tissue of interest or systemically. Nucleic acid sequences which encode PEDF polypeptides are known (see, e.g., published international patent applications WO 95/33480 and WO 93/24529); see also GenBank accession no. U29953), and others can be deduced from the polypeptide sequences discussed herein. Thus, PEDF expression vectors typically include isolated nucleic acid sequence which are homologous to known PEDF sequences, e.g., they will hybridize to at least a fragment of the known sequences under at least mild stringency conditions, more preferably under moderate stringency conditions, most preferably under high stringency conditions (employing the definitions of mild, moderate, and high stringency as set forth in Sambrook et al., 1989, Molecular Cloning: A Laboratory Manual, 2d edition, Cold Spring Harbor Press).

In addition to the nucleic acid encoding PEDF, an expression vector includes a promoter, and, in the context of the present invention, the promoter must be able to drive the expression of the PEDF gene within the cells. Many viral promoters are appropriate for use in such an expression cassette (e.g., retroviral ITRs, LTRs, immediate early viral promoters (IEp) (such as herpesvirus IEp (e.g., ICP4-IEp and ICP0-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters)). Other suitable promoters are eukaryotic promoters which contain enhancer sequences (e.g., the rabbit β-globin regulatory elements), constitutively active promoters (e.g., the β-actin promoter, etc.), signal and/or tissue specific promoters (e.g., inducible and/or repressible promoters, such as a promoter responsive to TNF or RU486, the metallothionine promoter, etc.), and tumor-specific promoters.

Within the expression vector, the PEDF gene and the promoter are operably linked such that the promoter is able to drive the expression of the PEDF gene. As long as this operable linkage is maintained, the expression vector can include more than one gene, such as multiple genes separated by internal ribosome entry sites (IRES). Furthermore, the expression vector can optionally include other elements, such as splice sites, polyadenylation sequences, transcriptional regulatory elements (e.g., enhancers, silencers, etc.), or other sequences.

The expression vector must be introduced into the cells in a manner such that they are capable of expressing the isolated nucleic acid encoding PEDF contained therein. Any suitable vector can be so employed, many of which are known in the art. Examples of such vectors include naked DNA vectors (such as oligonucleotides or plasmids), viral vectors such as adeno-associated viral vectors (Berns et al., 1995, Ann. N.Y. Acad. Sci. 772:95–104), adenoviral vectors (Bain et al., 1994, Gene Therapy 1:S68), herpesvirus vectors (Fink et al., 1996, Ann. Rev. Neurosci.19:265–287), packaged amplicons (Federoff et al., 1992, Proc. Natl. Acad. Sci. USA 89:1636–1640), papilloma virus vectors, picornavirus vectors, polyoma virus vectors, retroviral vectors, SV40 viral vectors, vaccinia virus vectors, and other vectors. In addition to the expression vector of interest, the vector can also include other genetic elements, such as, for example, genes encoding a selectable marker (e.g., β-gal or a marker conferring resistance to a toxin), a pharmacologically active protein, a transcription factor, or other biologically active substance.

Any vector selected must be capable of being produced in large quantities in eukaryotic cells. In addition, it is necessary that the vector can be constructed such that it is capable of being transferred into the cells of interest either with or without PEDF sequence, such that the vector which does not contain PEDF sequences serves as a control vector, which the vector which includes PEDF sequences is the experimental or therapeutic vector. Methods for manipulating the vector nucleic acid are well known in the art (see, e.g., Sambrook et al., supra) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The PEDF expression vector is introduced into the cells by any means appropriate for the transfer of DNA into cells. Many such methods are well-known in the art (Sambrook et al., supra; see also Watson et al., 1992, Recombinant DNA, Chapter 12, 2d edition, Scientific American Books). Thus, plasmids are transferred by methods such as calcium phosphate precipitation, electroporation, liposome-mediated transfection, gene gun, microinjection, viral capsid-mediated transfer, polybrene-mediated transfer, protoplast fusion, etc. Viral vectors are best transferred into cells by direct infection of the cells. However, the mode of infection may vary depending on the exact nature of the virus and the cell.

Cells into which the PEDF gene has been transferred under the control of an inducible promoter if necessary, can be used in the inventive method as transient transformants. Such cells themselves may then be transferred into a mammal for therapeutic benefit therein. Typically, the cells are transferred to a site in the mammal such that PEDF expressed therein and secreted therefrom contacts the desired endothelial cells in order that angiogenesis is inhibited. Alternatively, particularly in the case of cells to which the vector has been added in vitro, the cells may first be subjected to several rounds of clonal selection (facilitated usually by the use of a selectable marker sequence in the vector) to select for stable transformants. Such stable transformants are then transferred to a mammal for therapeutic benefit therein.

The PEDF may also be provided to the endothelial cells by transfecting into a population of other cells a vector comprising an isolated nucleic acid encoding PEDF, whereby the PEDF is expressed in and secreted from said other cells. The population of other cells so transfected is then transferred to a site in the mammal where PEDF so secreted contacts the endothelial cells and inhibits angiogenesis. Expression and secretion of PEDF from the other cells then has benefit on the endothelial cells. It is not necessary that the DNA encoding PEDF be stably integrated into the cells. PEDF may be expressed and secreted from non-integrated or from integrated DNA in a cell.

Within the cells, the PEDF gene is expressed such that the cells express and secrete the PEDF polypeptide. Successful expression of the gene can be assessed using standard molecular biological techniques (e.g., Northern hybridization, Western blotting, immunoprecipitation, enzyme immunoassay, etc.). Reagents for detecting the expression of PEDF genes and the secretion of PEDF from transfected cells are known in the art (see, e.g., published international patent applications WO 95/33480 and WO 93/24529); Steele et al., supra).

Depending on the location of the tissue of interest, PEDF can be supplied in any manner suitable for the provision of PEDF to endothelial cells within the tissue of interest. Thus, for example, a composition containing a source of PEDF (i.e., a PEDF polypeptide or a PEDF expression vector, or cells expressing PEDF, as described herein) can be introduced into the systemic circulation, which will distribute the source of PEDF to the tissue of interest. Alternatively, a composition containing a source of PEDF can be applied topically to the tissue of interest (e.g., injected, or pumped as a continuous infusion, or as a bolus within a tumor or intercutaneous or subcutaneous site, applied to all or a portion of the surface of the skin, dropped onto the surface of the eye, etc.).

Where the source of PEDF is a PEDF polypeptide (e.g., within a suitable composition), it is provided in a concentration and for a time sufficient to inhibit angiogenesis within the tissue.

The inhibition of angiogenesis is generally considered to be the halting of the development of new blood vessels, whether they develop be sprouting or by the arrival and subsequent differentiation into endothelial cells of circulating stem cells. However, since PEDF can induce apoptosis of activated endothelial cells, inhibition of angiogenesis in the context of the present invention should also be construed to include the killing of cells by PEDF, particularly cells in existing vessels near or within a tumor when activated by tumor angiogenesis factors. Thus, within the context of the present invention, inhibition of angiogenesis should be construed to include inhibition of the development of new vessels, which inhibition may or may not be accompanied by the destruction of nearby existing vessels.

Where PEDF is produced naturally, it can be present in concentrations as high as about 250 nM. Because PEDF is non-toxic, it can be supplied to tissues in a far more concentrated form. However, given PEDF's potency, it can be employed in the inventive method at far reduced concentrations, such as about 10 nM or less (e.g., as little as 0.01 nM). Indeed, in some protocols, about 2 nM PEDF or less effectively inhibits angiogenesis and endothelial cell migration. Depending on the formulation of a composition comprising the protein, it is supplied over a time course sufficient to retard angiogenesis within the desired tissue. In some protocols (e.g., where the PEDF is supplied to the surface of skin or to the eye), repeated application enhances the antiangiogenic effect and may be required in some applications. Where the source of PEDF is a PEDF expression vector, the cells expressing PEDF produce an effective amount of the protein (i.e., sufficient to inhibit angiogenesis in the tissue).

To facilitate the inventive method, the invention provides a pharmacological composition comprising a source of PEDF and a suitable diluent. In addition to the source of PEDF, the composition includes a diluent, which includes one or more pharmacologically-acceptable carriers. Pharmaceutical compositions for use in accordance with the present invention can be formulated in a conventional manner using one or more pharmacologically or physiologically acceptable carriers comprising excipients, as well as optional auxiliaries which facilitate processing of the active compounds into preparations which can be used pharmaceutically. Proper formulation is dependent upon the route of administration chosen. Thus, for systemic injection, the source of PEDF can be formulated in aqueous solutions, preferably in physiologically compatible buffers that may, if needed, contain stabilizers such as polyethylene glycol. For transmucosal administration, penetrants appropriate to the barrier to be permeated are used in the formulation. Such penetrants are generally known in the art. For oral administration, the source of PEDF can be combined with carriers suitable for inclusion into tablets, pills, dragees, capsules, liquids, gels, syrups, slurries, liposomes, suspensions and the like. For administration by inhalation, the source of PEDF is conveniently delivered in the form of an aerosol spray presentation from pressurized packs or a nebuliser, with the use of a suitable propellant. The source of PEDF can be formulated for parenteral administration by injection, e.g., by bolus injection or continuous infusion. Such compositions can take such forms as suspensions, solutions or emulsions in oily or aqueous vehicles, and can contain formulatory agents such as suspending, stabilizing and/or dispersing agents. For application to the skin, the source of PEDF can be formulated into a suitable gel, magma, creme, ointment, or other carrier. For application to the eyes, the source of PEDF can be formulated in aqueous solutions, preferably in physiologically compatible buffers. The source of PEDF can also be formulated into other pharmaceutical compositions such as those known in the art. A detailed discussion of pharmaceutical compositions and formulations is provided elsewhere herein.

Because it is known that PEDF is reduced or absent from some tumors, the invention also provides a method of assessing the prognosis of a tumor by assaying for the presence of PEDF within the tumor. The method involves obtaining tissue or fluid from the tumor and detecting the presence or absence of PEDF within the tissue or fluid. The tissue or fluid may be, for example, urine, plasma, serum, or vitreous or aqueous humor. The greater the PEDF concentration within the tumor correlates with a lesser likelihood that the tumor is undergoing angiogenesis. Thus, a higher PEDF concentration within the tumor is indicative of a relatively early stage of tumorigenesis and is, therefore, an optimistic indication. Conversely, the absence of PEDF within a given tumor, or the presence of a low level of PEDF, is indicative of a more advanced stage of tumerogenesis. Higher or lower levels of PEDF referred to herein, are measured in comparison with PEDF levels in an otherwise identical tissue obtained from normal, well individuals who do not have the disease in question.

Assessment of PEDF levels may be accomplished using assays which assess the levels of PEDF gene expression (e.g., via reverse transcriptase PCR (RT-PCR), Northern hybridization, in situ hybridization etc.). Alternatively, the presence of secreted PEDF may be measured in immunological assays, PEDF purification assays or PAGE analysis, etc.). Reagents for detecting the presence of PEDF within such tumors are known in the art (see, e.g., published international patent applications WO 95/33480 and WO 93/24529).

The invention also includes a kit comprising the peptide composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

In addition to all of the above, the invention should also be construed to include methods of regulating the expression of endogenous PEDF in a cell. For example, it is possible to upregulate PEDF production in a cell by inducing transient hyperoxia in the cell. Such treatment has the added benefit of downregulating inducers of angiogenesis. The invention should be construed to include the application of this method to each of the treatment modalities described herein.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "adjacent" is used to refer to nucleotide sequences which are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

As used herein, "alleviating a symptom" means reducing the severity of the symptom.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

An "mRNA-coding region" of a gene consists of the nucleotide residues of the coding strand of the gene and the nucleotide residues of the non-coding strand of the gene which are homologous with or complementary to, respectively, an mRNA molecule which is produced by transcription of the gene. It is understood that, owing to mRNA processing which occurs in certain instances in eukaryotic cells, the mRNA-coding region of a gene may comprise a single region or a plurality of regions separated from one another in the gene as it occurs in the genome. Where the mRNA-coding region of a gene comprises separate regions in a genome, "mRNA-coding region" refers both individually and collectively to each of these regions.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

A "disease" is a state of health of an animal wherein the animal cannot maintain homeostasis, and wherein if the disease is not ameliorated then the animal's health continues to deteriorate. A disease is "alleviated" if the severity of a symptom of the disease, the frequency with which such a symptom is experienced by a patient, or both, are reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity".

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264–2268), modified as in Karlin and Altschul (1993, Proc. Natl. Acad. Sci. USA 90:5873–5877). This algorithm is incorporated into the NBLAST and XBLAST programs of Altschul, et al. (1990, J. Mol. Biol. 215:403–410), and can be accessed, for example at the National Center for Biotechnology Information (NCBI) world wide web site having the universal resource locator "http://www.ncbi.nlm.nih.gov/BLAST/". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389–3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See http://www.ncbi.nlm.nih.gov.

The percent identity between two sequences can be determined using techniques similar to those described above, with or without allowing gaps. In calculating percent identity, typically exact matches are counted.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T".

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences".

As used herein, the term "promoter/regulatory sequence" means a nucleic acid sequence which is required for expression of a gene product operably linked to the promoter/ regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A first oligonucleotide anneals with a second oligonucleotide "with high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g. Sambrook et al., 1989, *Molecular Cloning: A Laboratory Manual*, Cold Spring Harbor Laboratory, New York).

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

A "substantially pure nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered. A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Modification and Synthesis of Peptides

The following section refers to the modification of peptides and to their synthesis. It will be appreciated, of course, that the peptides useful in the methods of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$–$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the biological activity of the peptide and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the methods of the invention.

The present invention also provides for analogs of proteins or peptides encoded by the nucleic acid disclosed herein. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

As noted above, modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The peptides of the present invention may be readily prepared by standard, well-established solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resincoupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use in the methods of the invention, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Pharmaceutical Compositions

Compounds which are identified using any of the methods described herein may be formulated and administered to a mammal for treatment of the diseases disclosed herein are now described.

The invention encompasses the preparation and use of pharmaceutical compositions comprising a compound useful in the methods of the invention as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Sustained release compositions comprising PEDF may be particularly useful. For example, sustained release compositions may be used in the vitrous and may also be used behind the eye. As stated elsewhere herein, sustained release compositions may also be useful in systemic or other delivery routes for administration of PEDF. One of ordinary skill in the art will know the appropriate sustained release compositions which can be used to treat the desired disease to achieve the desired outcome.

Typically dosages of the compound of the invention which may be administered to an animal, preferably a human, range in amount from 1 $\mu$g to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

The procedures employed in these examples, such as cell culture, manipulation of protein and DNA, etc. are well known in the art (see generally Sambrook et al., supra). Accordingly, in the interest of brevity, the experimental protocols are not discussed in detail.

Example 1

The data presented herein demonstrate that PEDF prevents endothelial cell migration.

The migration of different vascular endothelial cell types was determined by adding PEDF to cultured endothelial cells, specifically, endothelial cells isolated from bovine adrenal capillaries, human umbilical chords, and human dermal microvascular tissue.

The cells were plated on gelatinized Nucleopore membranes (5 μm pores for bovine capillary cells and 8 μm pores for other cells) in an inverted modified Boyden chamber. After two hours, the chamber was reinverted and test substances added to the top wells of each. Specifically, populations were exposed to either culture medium alone (control), 10 ng/ml bFGF, 2 nM PEDF (full length PEDF), or both 10 ng/ml bFGF (basic fibroblast growth factor) and 10 nM PEDF. The cells were then permitted to migrate for 3–4 hours. Following this, the membranes were fixed and stained, and the number of cells that had migrated were counted.

The results of the assay are presented in FIG. 1 as a percentage of maximal migration (error bars represent standard error measurement, n=4). As is depicted, all three types of vascular endothelial cells exhibited nearly 100% migration in the presence of bFGF. However, in the presence of PEDF, considerably less migration was observed. These results demonstrate that PEDF inhibits endothelial cell migration. These results are surprising, given that the PEDF protein is known to induce neural differentiation of cultured retinoblastoma tumor cells, to be a neurotrophic factor for cerebellar granular cells and a cytostatic factor for glial cells (Taniwaki et al., 1997, J. Neurochem. 68:26–32; Sugita et al., 1997, J. Neurosci. Res. 49:710–718; Tombran-Tink et al., 1991, Exp. Eye Res. 53:411–414; Becerra, 1997, Structure-Function Studies on PEDF," Chapter 21, in Chemistry and Biology of Serpins, Church et al., eds., Plenum Press).

Example 2

The data presented herein demonstrate that the prevention of cell migration by PEDF is specific for endothelial cells.

The ability of PEDF to prevent migration of fibroblasts or smooth muscle was tested using cells obtained from human diploid fibroblast cell line WI-38, human foreskin fibroblasts, vascular smooth muscle, and normal human neutrophils.

The assay was performed as indicated in Example 1, except that the dose of PEDF varied from 0.01 nM to about 50 nM and that the migration assay was performed without inverting the chambers. Moreover, the inducer of migration varied with the cell type (IL-8 was used at 1 μg/ml and PDGF was used at 250 pg/ml).

The results of this experiment are presented in FIGS. 2A–2D. As indicated in these figures, PEDF did not inhibit migration of any of the cell lines. This result indicates that the antimigratory activity of PEDF is specific for vascular endothelial cells.

Example 3

The data presented herein demonstrate that PEDF is among the most potent inhibitors of endothelial cell migration when compared with other antiangiogenic factors.

Using a protocol similar to that outlined in Example 1, bovine adrenal capillary endothelial cells were exposed to bFGF, PEDF, and several known antiangiogenic factors. The amount of a given factor necessary to achieve 50% of migration was determined and is reported here as $ED_{50}$. A smaller $ED_{50}$ measurement indicates a more potent antiangiogenic factor. The results of this experiment, presented in Table 1, indicate that PEDF is a highly potent antiangiogenic factor.

TABLE 1

| Agent | $ED_{50}$ (nM) |
| --- | --- |
| PEDF | 0.1–0.5 |
| Thrombospondin | 0.5 |
| Endostatin | 3.0 |
| Angiostatin | 3.5 |
| Retinoic Acid | 15 |
| Tissue Inhibitor of Metalloproteinase-1 | 3500 |
| Captopril | 10,000 |

Example 4

These data demonstrate that PEDF inhibits the angiogenic activity of known angiogenic agents.

Using a protocol similar to that outlined in Example 1, bovine adrenal capillary endothelial cells were exposed to five known angiogenic agents alone or in combination with 0.1 μg/ml PEDF. In particular, aFGF was employed at a concentration of 50 ng/ml, bFGF was employed at a concentration of 10 ng/ml, IL-8 was employed at a concentration of 40 ng/ml, PDGF was employed at a concentration of 250 pg/ml, and VEGF was employed at a concentration of 100 pg/ml.

Figure 3:
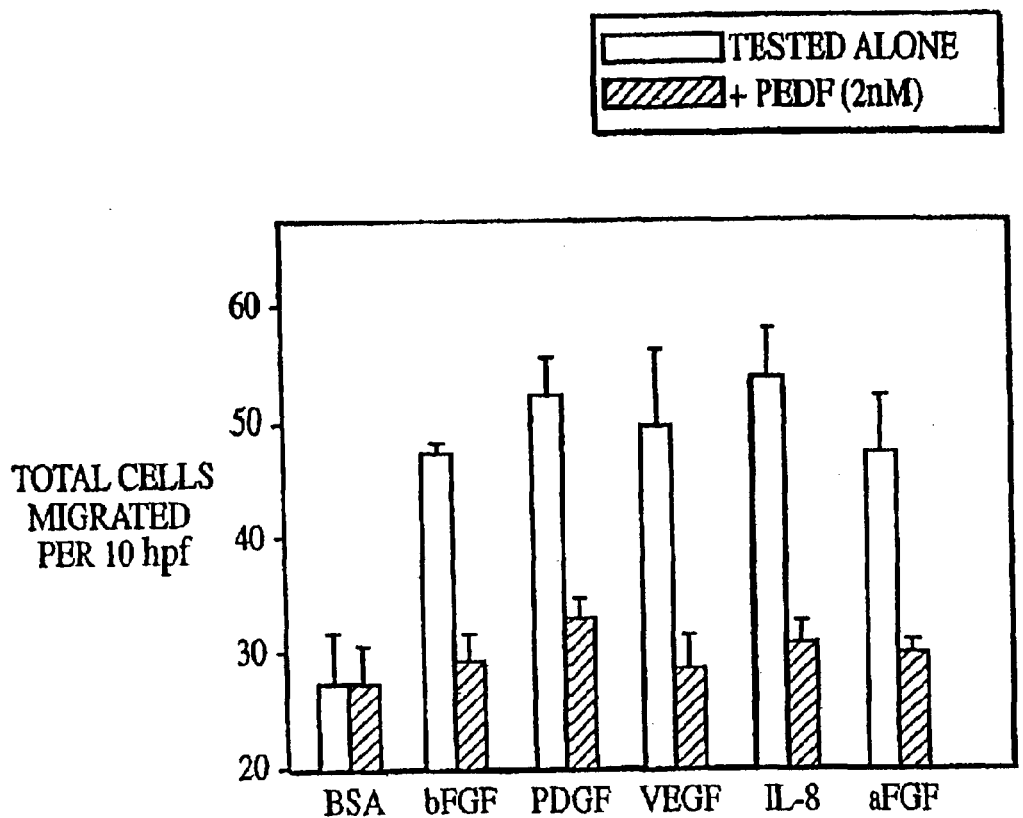
FIG. 3 is a graph which demonstrates the ability of PEDF to prevent the migration of capillary endothelial cells towards a variety of different inducers of angiogenesis including basic fibroblast growth factor (bFGF), platelet derived growth factor (PDGF), vascular endothelial cell growth factor (VEGF), interleukin-8 (IL-8), and acidic fibroblast growth factor (aFGF).

The results of the assay are presented in FIG. 3. As is depicted, the migration of the cells was considerably inhibited by PEDF, regardless of the angiogenic agent. These results demonstrate that PEDF-mediated inhibition of vascular endothelial migration is not specific for bFGF induction, but that PEDF acts generally to inhibit migration of these cells.

Example 5

These data demonstrate that PEDF inhibits neovascularization in vivo.

Pellets comprising various proteins were implanted in the avascular corneas of rats. Pellets either contained or lacked bFGF, and also contained either PEDF, or bovine serum albumin (BSA) which functioned as a control. After seven days, the corneas of the rats were examined to determine whether angiogenesis had occurred.

The results of this assay are presented in Table 2. As indicated, no vascularization was observed from injecting pellets lacking bFGF. However, vascularization was observed in all eyes implanted with bFGF and BSA. Further, co-injection of bFGF and PEDF resulted in no neovascularization in any cornea. These results indicate that PEDF is a potent inhibitor of angiogenesis in vivo.

TABLE 2*

| Treatment | Without bFGF | With bFGF |
| --- | --- | --- |
| PEDF (8 nM) | 0/3 | 0/3 |
| BSA | 0/2 | 4/4 |

*results expressed as number of corneas with angiogenesis/number of corneas implanted.

Example 6

The data presented herein demonstrate that PEDF polypeptides other than the full PEDF protein are active antiangiogenic agents.

Trypsin digestion of the complete PEDF protein cleaves the protein at amino acid 352 of SEQ ID NO:1, removing the approximately 3–5 kDa carboxy-terminal portion of the protein (Becerra et al., 1995, J. Biol. Chem. 270:25992–25999). This procedure was employed to generate the fragments, and the truncated N-PEDF fragment (representing amino acids 21–382 of SEQ ID NO:1) was purified from trypsin by heparin affinity chromatography.

Figure 4:
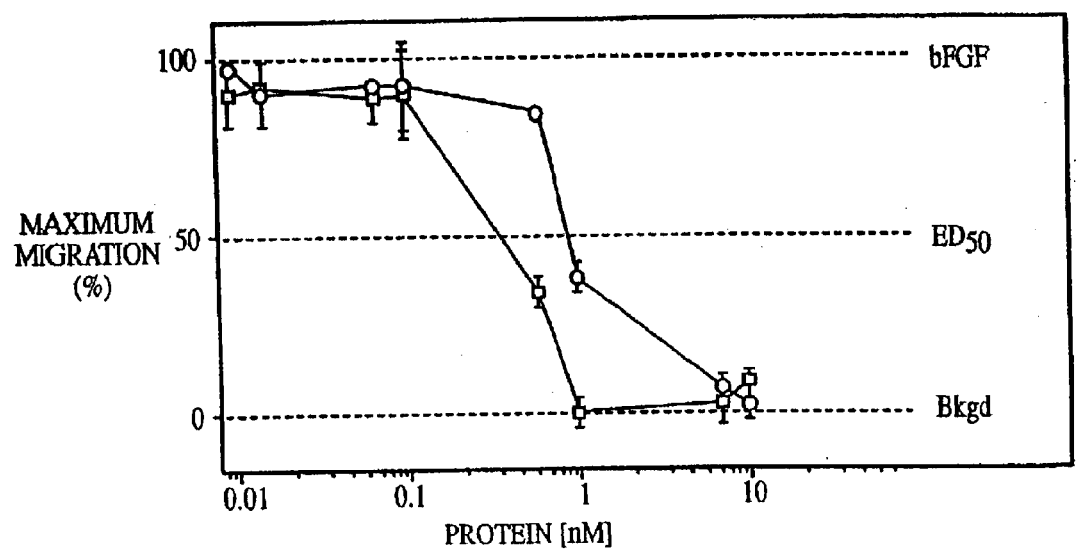
FIG. 4 is a graph of a dose response curve representing the antiangiogenic activity of full length PEDF (filled circles) showing it to be active at sub-nanomolar concentrations in the inhibition of capillary endothelial cell migration towards bFGF and to be more active than another inhibitor of angiogenesis, angiostatin (empty circles).
Figure 5:
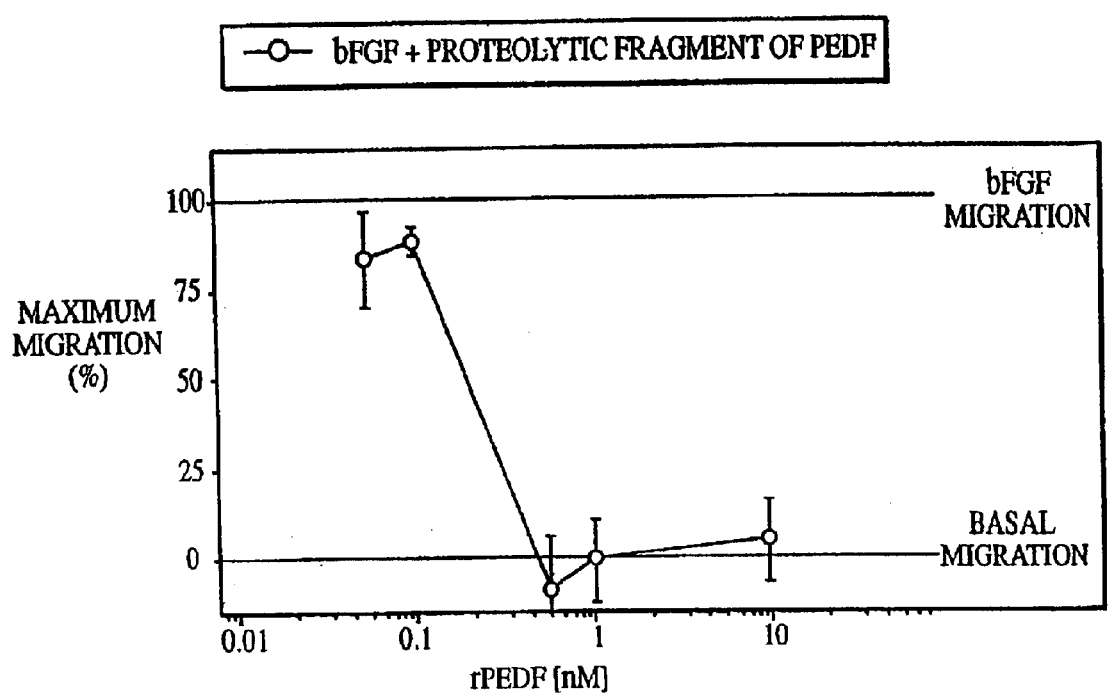
FIG. 5 is a dose-response curve representing the antiangiogenic activity of a truncated PEDF polypeptide which is missing 5 kDa from the C-terminal end, indicating that fragments of PEDF retain full activity.

Using a protocol similar to that outlined above, various concentrations of either full length PEDF or the truncated peptide were assessed for their respective abilities to affect endothelial cell migration. Data generated for the truncated peptide are indicated in FIG. 5. Comparison of these data with the activity of the full length PEDF (see FIG. 4) reveals both proteins to be similarly potent at inhibiting endothelial cell migration. These results indicate that peptides other than full length PEDF are active PEDF polypeptides.

Figure 7A:
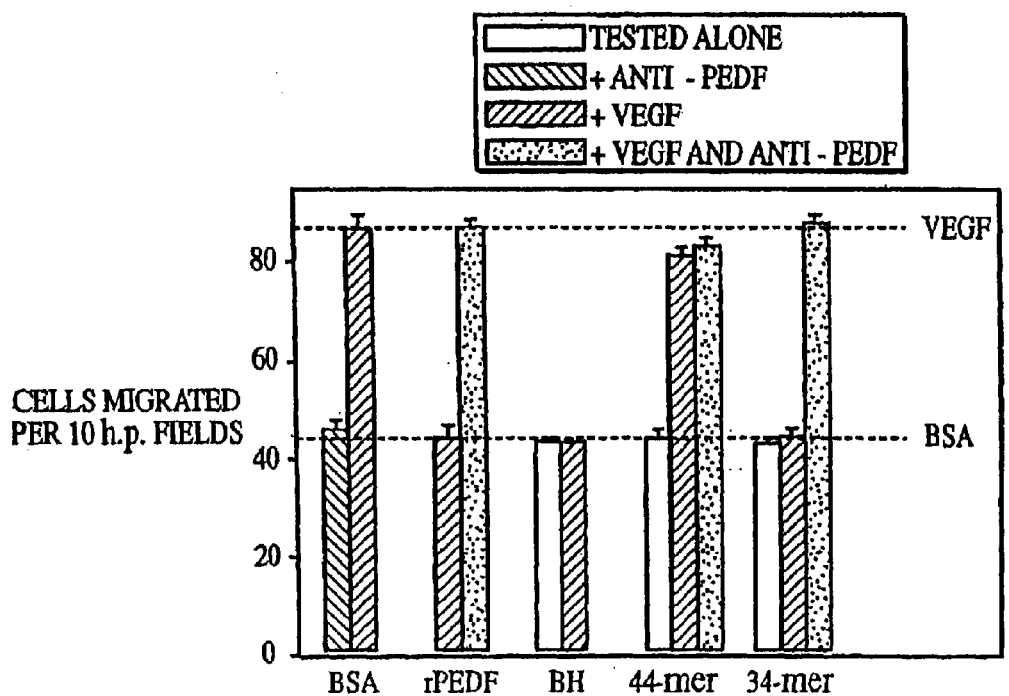
FIGS. 7A and 7B, are two graphs which depict the effect of various truncated peptides derived from PEDF on angiogenesis.
Figure 7B:
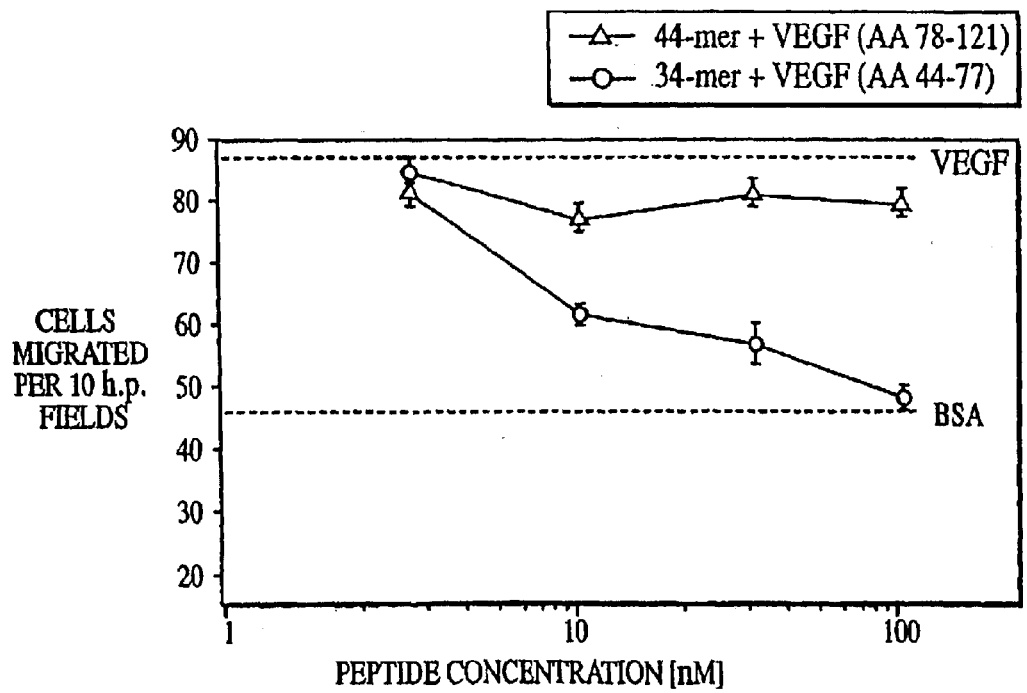

Additional truncated peptides derived from PEDF were tested for efficacy in the endothelial cell migration assay using human dermal microvascular endothelial cells (Clonetics, Cell Systems) at passage 9 in a modified Boyden Chamber, as described above, and the results are shown in FIG. 7. In FIG. 7A, the cells were exposed to the gradient of VEGF in the presence of purified recombinant PEDF (rPEDF), bacterially produced PEDF (BH) or PEDF peptides containing only amino acid residues 78–121 (44-mer) and 44–77 (34-mer) referring to SEQ ID NO:1. Neutralizing antibodies were added where shown to verify if the anti-angiogenic effect is specific to PEDF peptides and not due to contamination. Both full length PEDF preparations were used at 25 nM, neutralizing polyclonal antiserum against PEDF was used at 1:200 dilution, recombinant human VEGF (R&D Systems) at 200 pg/ml. In FIG. 7B, the cells were exposed to the gradient of VEGF in the presence of increasing concentrations of 34-mer and 44-mer peptides. The antiserum used in this experiment was not affinity purified, whereas the antiserum used in all other experiments presented herein was affinity purified.

The data establish that a 34 amino acid peptide fragment of the 418 amino acid PEDF protein has anti-angiogenic activity. This peptide blocked the migration of capillary endothelial cells towards an inducer, VEGF. Further, the data demonstrate that the activity of the 34 amino acid peptide could be abrogated by addition of polyclonal antibodies specific for two peptides, one of which was contained within the 34-mer. This peptide has an ED50 of about 10 nM. This is unusually active for a small peptide as most peptides have an ED50 in the $\mu$M range rather than the nM range. The ED50 for the intact PEDF is about 0.3 nM. Because of its unusual potency this peptide may be particularly useful in the methods of the invention and for the development of a therapeutic compound capable of affecting angiogenesis.

These data also differentiate the region of PEDF that is anti-angiogenic from the region which induces differentiation in retinoblastoma tumor cells and that which is neurotrophic. It has been shown by (Alberdi et al., 1999, J. Biol. Chem. 274:31605–31612), that these latter two traits are not induced by the 34 amino acid peptide discovered herein, but by an adjacent peptide fragment of PEDF that does not overlap with the 34 amino acid peptide. Thus, in the methods of the invention, should it be the case that the neural activities of PEDF cause complications during angiogenic therapy, such complications may be avoided by using the 34 amino acid peptide fragment of PEDF. This finding is exemplified in FIG. 7 wherein it is shown that the 34 amino acid peptide, representing amino acids 44 to 77 in the PEDF protein, was active as an anti-angiogenic agent whereas the adjacent 44 amino acid peptide comprising amino acids 78 to 121 was not active as an anti-angiogenic agent.

Example 7

These data demonstrate that exogenous PEDF applied to the skin promotes the growth of hair therein.

In additional experiments, injections of purified histidine-tagged PEDF resulted in increased hair follicle density and the growth of a tuft of hair in the skin of athymic (nude/nude) mice that are naturally hairless. This result suggests that PEDF has the potential for stimulating new hair growth.

PEDF is a protein expressed by many cell types including cells present in hair follicles (pilo sebacious gland). An increase in hair follicle density was observed in the skin overlying experimentally produced neuroblastoma tumors that were injected daily for four consecutive days with purified PEDF. This was not observed in the skin of control animals whose tumors were similarly injected with saline vehicle.

The treatment consisted of injecting a total of 2 $\mu$g of purified histidine-tagged PEDF in a volume of 100 $\mu$l of phosphate buffered saline into 2–3 sites/tumor each day for 4 consecutive days. On the fifth day, a small area of increased hair growth was noticed over the injection sites. The mice were euthanized using an overdose of metaphane, and the tumors were surgically removed. Tumor tissue was sliced and placed in buffered formalin for at least 24 hours. Tissue was embedded in paraffin and prepared for histologic examination. The skin overlying neuroblastoma tumors treated with PEDF had increased hair follicle density when compared with the skin overlying tumors injected with saline vehicle (FIG. 8). Similar increases in hair follicle density have been seen in the absence of tumors following injection of purified PEDF.

Example 8

The data presented herein depict the fact that PEDF triggers differentiation of neuroblastoma tumors, thereby providing the basis for treatment of these tumors. In vitro treatment of neuroblastoma cells, and in vivo treatment of experimentally produced neuroblastoma tumors with purified histidine tagged-PEDF protein triggered differentiation of the cells. These data therefore suggest that administration of PEDF to these cells is an effective means for induce these tumors to differentiate and therefore grow more slowly.

PEDF is a protein expressed and secreted by many cell types including Schwann cells. Neuroblastomas are malignant tumors, and the presence of Schwann cells within these tumors is associated with better outcomes. The data presented herein indicate that one of the reasons the presence of Schwann cells leads to a favorable prognosis for neuroblastoma tumors is the fact that these cells produce PEDF. The PEDF produced therein acts in a paracrine fashion on the tumor cells to induce their differentiation. Since differentiated neuroblastoma cells grow more slowly, if at all, the administration of PEDF to neuroblastoma tumors provides a novel therapy for this tumor by slowing the growth of the cells. Cell growth is slowed in two ways, (1) by binding of PEDF to endothelial cells that form the blood vessels feeding the tumor and preventing their growth and thereby indirectly inhibiting the tumor, and (2) by binding of PEDF directly to the tumor cells thereby inducing their differentiation.

In vitro experiments were conducted to verify the effect of PEDF on cell lines derived from neuroblastoma tumors. Two neuroblastoma derived cell lines were obtained from the American Tissue Type and Culture, SK-N-BE(2) and SK-N-SH. Both cell lines were maintained in culture in DMEM containing 10% fetal bovine serum (Flow Laboratories, McLean, Va.) in 37° C. and 5% $CO_2$. Cells ($1.25 \times 10^4$/ml) were resuspended, and 1 ml/well was used to seed 24 well plates. Twenty-four hours later, PEDF was added to triplicate wells at 0, 0.1, 0. , 0.75, 1 or 10 nM, and the cells were incubated for an additional 24 hours. The percentage of differentiated cells was determined by counting the total number of cells in three non-overlapping 1 $mm^2$ areas per well. A cell was considered differentiated if it possessed neurite outgrowths greater than 50 microns in length.

Figure 9A:
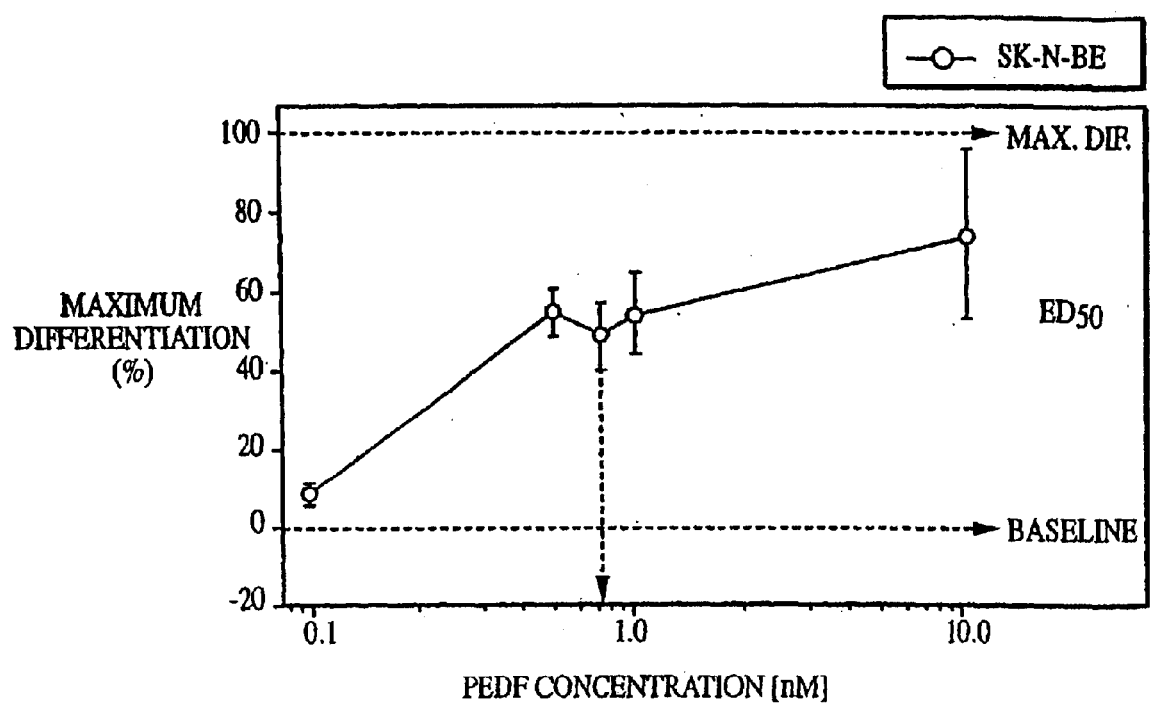
FIGS. 9A and 9B, is a series of graphs depicting the increased differentiation of cultured human neuroblastoma cells (SK-N-BE in FIG. 9A and SK-N-SH in FIG. 9B) when the cells were treated for twenty four hours with the indicated concentration of purified PEDF. Downward arrows indicate the dose that induced differentiation in 50% of treated cells.
Figure 9B:
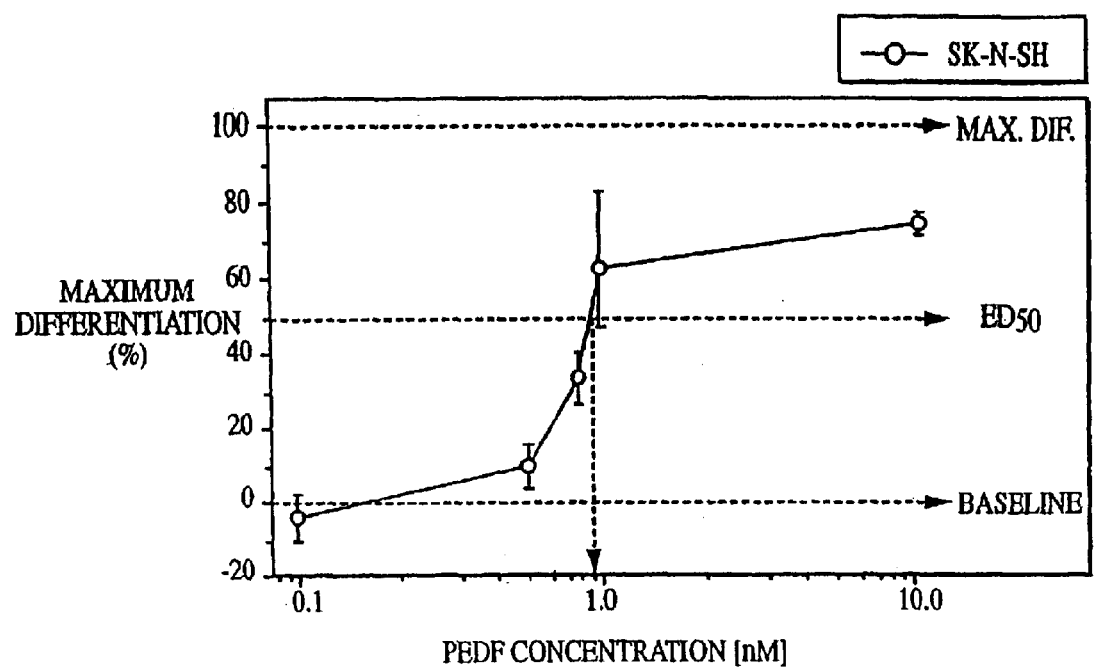

The results are presented in FIGS. 9A and 9B, and photographs of control and PEDF treatment groups are shown in FIG. 10. In addition, when an antibody raised against PEDF derived peptide that is capable of neutralizing PEDF activity in angiogenesis assays was added to cells, it effectively blocked PEDF-triggered differentiation (FIG. 10).

In vivo experiments were conducted to determine the effect of PEDF on neuroblastoma tumors. Human neuroblastomas were experimentally induced in athymic (nu/nu) mice by injecting $1 \times 10^6$ SK-N-BE(2) cells subcutaneously into 2 sites on the hind flanks of each mouse. When the tumors grew to a palpable size (approximately 8 mm in diameter) PEDF treatment was started. A total of 2 μg of purified histidine-tagged PEDF in a volume of 100 μl of phosphate buffered saline was injected into 2-3 sites/tumor each day for 4 consecutive days. On the fifth day, the mice were euthanized by an overdose of metaphane, and the tumors were surgically removed. Tumor tissue was sliced and placed in buffered formalin for at least 24 hours. Tissue was embedded in paraffin and prepared for histologic examination. Sections were stained with an antibody that recognized neurofilament protein (Dako, Carpinteria, Calif.). Neuroblastoma tumors treated with PEDF exhibited increased differentiation as determined by acquisition of positive staining for neurofilament protein (FIG. 11). A total of six SK-N-BE(2) tumors were treated with PEDF and 6/6 were moderately to strongly positive for neurofilament staining. A total of 4 tumors were treated with PBS and all were negative or exhibit focal staining of single cells with more abundant cytoplasm (FIG. 11).

Example 9

The data presented in this example provides evidence that PEDF is the major inhibitor of angiogenesis in the vitreous and in the cornea of human and mouse eyes and is controlled by oxygen tension in vitro and in vivo.

In the absence of disease the vasculature of the mammalian eye is quiescent, due to the presence of natural inhibitors of angiogenesis. In the present invention, PEDF is demonstrated to be responsible for preventing vessels from invading the cornea and for the normal anti-angiogenic activity of the vitreous. In the experiments presented herein, the secretion of PEDF by retinal cells was increased in low oxygen and decreased in high oxygen, suggesting that its loss plays a permissive role in retinal neovascularization. Thus, PEDF is useful as a therapeutic for treatment of the eye, especially in ischemia-driven retinopathies where pathological neovascularization compromises vision and leads to blindness.

Angiogenesis, the growth of new blood vessels from preexisting ones, is under tight regulation in most healthy tissues where the influence of naturally occurring inhibitors prevents new vessel growth (Bouck et al., 1996, Adv. Cancer 69:135; Hanahan and Folkman, 1996, Cell 86:353). The disruption of such controls plays an essential role in the development of a variety of diseases, from arthritis to cancer (Folkman et al., 1995, Molecular Basis of Cancer 206–232). In the healthy mammalian eye, vessels are normally excluded from the cornea and from the vitreous, both compartments that have been shown to have anti-angiogenic activity (Brem et al., 1977, Am. Ophthalmol. 84:323; Henkind, 1978, Am. Ophthalmol. 85:287; Kaminska and Niederkom, 1993, Invest. Opthalmol. Vis. Sci. 34:222). Failure to bar vessels from the cornea is associated with loss of visual acuity. opacification and abnormal healing (Kaminska and Niederkom, 1993, Invest. Opthalmol. Vis. Sci. 34:222). In the retina, excessive neovascularization underlies ischemic retinopathies such as proliferative diabetic retinopathy as well as age related macular degeneration, currently the leading causes of loss of sight in the western world. Data presented below identify the retinal protein pigment epithelium-derived factor (PEDF) as an exceptionally potent new inhibitor of angiogenesis and as a molecule responsible for the long-recognized anti-angiogenic activity of the healthy vitreous and cornea.

In studies aimed at identifying antiangiogenic factors in the eye that might be regulated by the retinoblastoma tumor suppressor gene (Rb), media was fractionated where the media was previously conditioned by a retinoblastoma cell line that had been infected with a retrovirus expressing the wild-type Rb gene, WERI-Rb-27R. (Xu et al., 1991, Cancer Res. 51:4481). A protein purification scheme resulted in a 1000- to 1250-fold enrichment of antiangiogenic activity and a single 50-kD band on a silver-stained protein gel. PEDF was purified from WERI-Rb-27R serum-free conditioned media by sequential steps consisting of dialysis (molecular mass cutoff, 30 kD) against distilled water, 60 to 95% ammonium sulfate precipitation, step elution from lentil lectin Sepharose 4B (Pharmacia) with 0.5 M α-methyl-D-mannopyranoside, and elution from a HiTrap heparin Sepharose column (Pharmacia) with increasing NaCl gradient. (Xu, et al., 1991, Cancer Res. 51:4481). Purification was monitored by an endothelial cell migration assay, and the yield was 17.5%. Migration assays were performed in quadruplicate for each sample with bovine adrenal capillary endothelial cells or human dermal microvascular endothelial cells (Clonetics, San Diego, Calif.) as described. (Polverini, et al., 1991, Methods Enzymol. 198:440). To combine multiple experiments, background migration (Bkgd) was first subtracted toward vehicle (0.1% bovine serum albumin) and them normalized data by setting maximum migration toward inducer alone to 100%. All experiments were repeated two to five times. Statistics were performed on raw data before normalization with the Student's t test. Standard errors were converted to percentages. Edman degradation of proteolytically derived internal peptides of the protein yielded two unambiguous sequences (TSLEDFYLDEERTVRVPMMXD (SEQ ID NO: 3) and IAQL-PLTGXM (SEQ ID NO: 4)). Single-letter abbreviations for the amino acid residues are as follows: A, Ala; D, Asp; E. Glu; F. Phe; G, Gly; I, Ile; L, Leu; M, Met; P, Pro; Q, Gln; R, Arg; S, Ser; T, Thr; V, Val; X, any amino acid; and Y, Tyr. A BLAST protein homology search revealed that PEDF contains identical sequences. Protein microsequence analysis showed that this protein was identical to the previously described pigment epithelium-derived factor (PEDF).

Figure 12A:
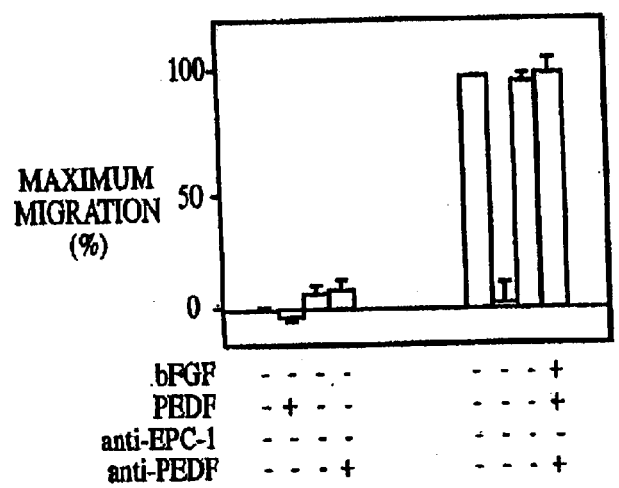
FIGS. 12A–12C, is a series of graphs depicting the inhibitory activity of purified PEDF on migration of cultured endothelial cells and the requirement of PEDF for antiangiogenic activity of human vitreous fluid and corneal extracts.

PEDF was first purified from the conditioned media of human retinal pigment epithelial cells as a factor that induced neuronal differentiation of cultured Y79 retinoblastoma cells. (Beccerra, Chemistry and Biology of Serpins, Church, et al., Eds. (Plenum, N.Y., 1997), pp. 223–237). (Tombran-Tink, et al., 1991, Exp. Eye Res. 53:411 1991; Steele et al., 1993, Proc. Natl. Acad. Sci. U.S.A. 90:1526). PEDF is neurotrophic for cerebellar granule cells, inhibits microglial growth, and is also referred to as early population doubling level cDNA (EPC-1), reflecting its up-regulation during cell cycle phase Go in young but not in senescing cultured fibroblasts. (Tanawaki, et al., 1995, J. Neurochem. 64:2509; Y. Sugita et al., 1997, J. Neurosci. Res., 49:710). Pignolo, et al., 1993, J. Biol. Chem. 268:8949 1993); (Tombran-Tink, et al., J. Neurosci., 15:4992 1995). The protein shares sequence and structural homology with the serine protease inhibitor (Serpin) family but does not inhibit proteases. (Becerra, et al., 1993, J. Biol. Chem. 268:23148 1993); Becerra, et al., 1995 ibid. 270:25992). The antiangiogenic activity purified from WERI-Rb-27R conditioned media was likely due to PEDF and not to a minor containment, as it was retained when the protein was recovered as a single band from an SDS-polyacrylamide gel (Dawson, et al., unpublished data) and it was neutralized by antibodies raised against either recombinant PEDF or a PEDF peptide. (FIG. 12A).

Biochemically purified as well as recombinant forms of PEDF potently inhibited neovascularization in the rat cornea (FIGS. 13A and 13B). Human PEDF cDNA was engineered by polymerase chain reaction to encode a COOH-terminal hexahistidine tag, cloned into pCEP4 (Invitrogen, Carlsbad, Calif.), and transfected into human embryonic kidney cells. Recombinant PEDF was purified from the conditioned media with the Xpress Protein Purification System (Invitrogen, Carlsbad, Calif.). In vitro, PEDF inhibited endothelial cell migration in a does-dependent manner with a median effective dose ($ED_{50}$) of 0.4 nM (FIG. 12B), placing it among the most potent natural inhibitors of angiogenesis in this assay (see supplemental figures, available at www.sciencemag.org/feature/data/104007), slightly more active than pure angiostatin (FIG. 12B), thrombospondin-1 ($ED_{50}$ of 0.5nM), and endostatin (ED50 of 3 nM). At doses of 1.0 nM or greater, PEDF also inhibited basic fibroblast growth factor (bFGF)-induced proliferation of capillary endothelial cells by 40%.

PEDF inhibited endothelial cell migration toward every angiogenic inducer we tested, including platelet-derived growth factor, vascular endothelial growth factor (VEGF), interleukin-8, acidic fibroblast growth factor, and lysophosphatidic acid. (See supplemental figures, available at www.sciencemag.org/feature/data/1040070). It showed some specificity for endothelial cells, inhibiting the migration of microvascular cells cultured from the bovine adrenal gland or human dermis and those from the umbilical vein. In contrast, it did not inhibit the migration of human foreskin or lung fibroblasts, aortic smooth muscle cells, oral keratinocytes, or neutrophils toward stimulatory cytokines, even when PEDF was present at concentrations 10 times that needed to inhibit endothelial cells. (See supplemental figures, available at www.sciencemag.org/feature/data/1040070).

Figure 12B:
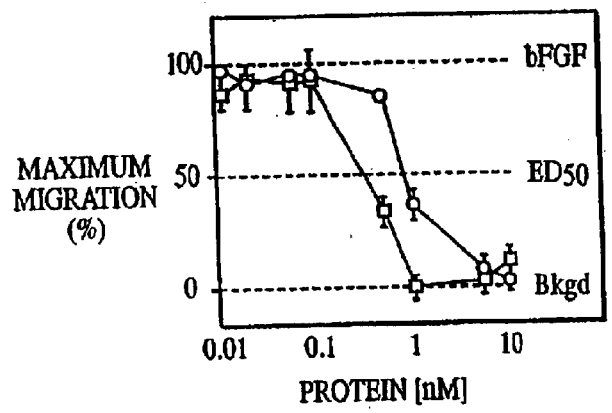
Figure 12C:
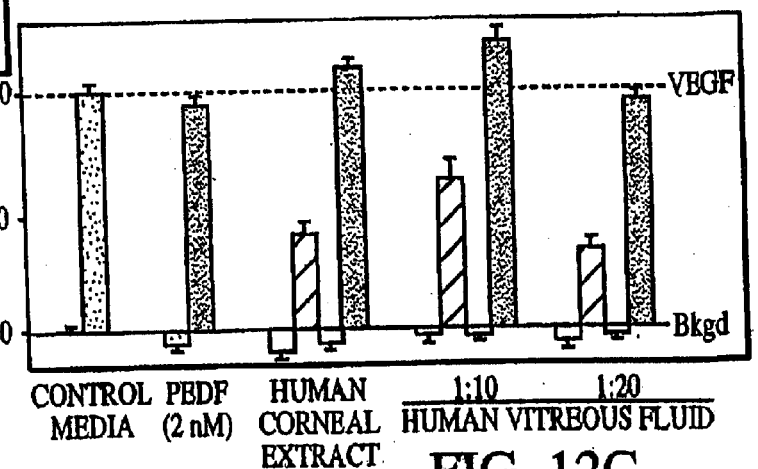

Neutralizing PEDF antibodies reduced the inhibition of endothelial cell chemotaxis by stromal extracts (Klintworth, 1991, Corneal Angiogenesis: A Comprehensive Critical Review (Springer-Verlag, New York); Kaminska and Niederkorn, 1993, Investig. Opthalmol. Vis. Sci. 34:222) prepared from human (FIG. 12C), mouse, and bovine corneas. For preparation of stromal extract, corneas were freed of associated epithelium and as much of the endothelium as possible, washed extensively in ice-cold phosphate-buffered saline (PBS, pH 7.4), and minced into small fragments that were incubated for 24 hours in PBS containing 0.5 MM phenylmethanesulfonyl fluoride. The extract was filer sterilized, stored at −80° C., and tested in migration assays at a final concentration of 10 µg of protein per milliliter. Similarly, removal of PEDF and antibody linked to protein A beads completely eliminated the antiangiogenic activity in bovine and human stromal extracts (FIGS. 13A and 13B). Furthermore, addition of neutralizing antibodies to PEDF, in the absence of exogeneous angiogenic inducers, stimulated the invasion of new vessels into the rat cornea (FIGS. 12A and 12B). This appeared to be due to local blockade of PEDF, which unmasked endogenous angiogenic stimulatory activity in the cornea (FIGS. 12C, 13A and 13B). Antibody to PEDF alone did not stimulate endothelial cell migration in vitro (FIG. 12A), and no neovascularization was observed in rat corneas when the antibody was preincubated with the PEDF peptide 327 to 343 against which it was raised (FIGS. 13A and 13B). The PEDF peptide alone was neutral in angiogenic assays (FIG. 13A).

Like the cornea, the vitreous humor is antiangiogenic (Brem, et al., 1977, Am. J. Ophthalmol. 84:323; Henkind 1978 ibid. 85:287) and generally devoid of vessels, and it also contains high concentrations of PEDF (Beccerra, 1997, Chemistry and Biology of Serpins; Church, et al., 1997, Eds (Plenum, New York) pp. 223–237); Wu and Beccerra, 1996, Investig. Ophthalmol. Vis. Sci. 37:1984). It was discovered that removal of PEDF from vitreous fluid abrogated its antiangiogenic activity and revealed an underlying angiogenic stimulatory activity (FIGS. 12C, 13A and 13B). The level of PEDF in the vitreous was sufficient to inhibit endothelial cell migration even in the presence of 4 ng of VEGF per milliliter of vitreous, a concentration similar to that found in vitreous fluid obtained from patients with proliferative diabetic retinopathy (Aiello, et al., 1994, N. Engl. J. Med. 331:1480; Adamis, et al., 1994, Am. J. Ophthalmol. 118:445). Transforming growth factor β (TGFβ) has been postulated to be an inhibitor of ocular neovascularization (Ogata et al., 1997, Curr. Eye Res. 16:9; Hayasaka, et al., 1998, Life Sci. 63:1089; Vinores, et al., 1998, J. Neuroimmunol. 89:43). However, in our experiments, neutralization of TGFβ isoforms 1, 2, and 3 did not alter the antiangiogenic activity of vitreous fluid or corneal extracts in vitro (see supplemental figures, available at www.sciencemag.org/feature/data/1040070) or induce corneal neovascularization in vivo (FIG. 13A).

In neonates, changes in ambient oxygen concentration can regulate the vascular density of the retina. This effect is usually attributed to changes in the level of the angiogenic inducer VEGF, which is up-regulated when oxygen is limiting and down-regulated when it is in excess (Aiello, et al., 1995, Proc. Natl. Acad. Sci. U.S.A. 92:10457; Adamis, et al., 1996, Arch. Ophthalmol. 114:66; Provis, et al., 1997, Exp.

Figure 14A:
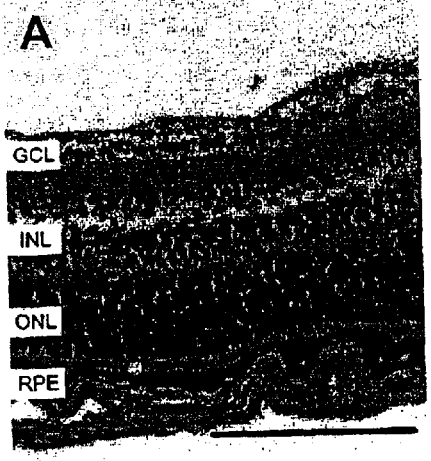
FIGS. 14A–14F, is a series of images of photomicrographs depicting induction of PEDF protein expression by hyperoxia in the neonatal mouse. Retinas were harvested as postnatal day 12 (P 12) (FIGS. 14A and 14B), P18(c), or P21 (FIG. 14D) from C57BL/6 mice that had been maintained at ambient oxygen (FIGS. 14A, 14C, and 14D) or exposed to 75% oxygen from P7 to P12 (FIG. 14B) and stained for PEDF. Note accumulation of PEDF (arrowheads), as indicated by reddish-brown color. Control sections directly adjacent to FIG. 14D were stained without primary antibody (FIG. 14E) or after preincubation of primary antibody with PEDF peptide 327 to 343 (FIG. 14F). Retina layers indicated in FIG. 14A include retinal pigment epithelium (RPE), outer nuclear layer (ONL), inner nuclear layer (INL), and ganglion cell layer (GCL). Mouse eyes were fixed in formalin within 1 to 5 min of harvest. For immunostaining, paraffin-embedded sections were incubated with anti-PEDF and visualized with ABC methods (Vectastain Elite; Vector Labs, Burlingame, Calif.). Scale bar, 25 μm PEDF antipeptide antibody (anti-PEDF) was raised in rabbits against two polypeptides containing PEDF amino acids 327 to 343 and amino acids 55 to 71 conjugated to Keyhole-limpet hemocyanin. It was affinity-purified on a column containing the peptide with amino acids 327-343. All protein and antibodies were extensively dialyzed against PBS before use in biological assays.
Figure 14B:
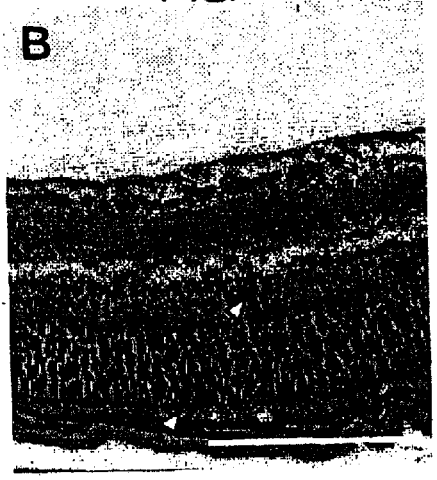
Figure 14C:
Figure 14D:
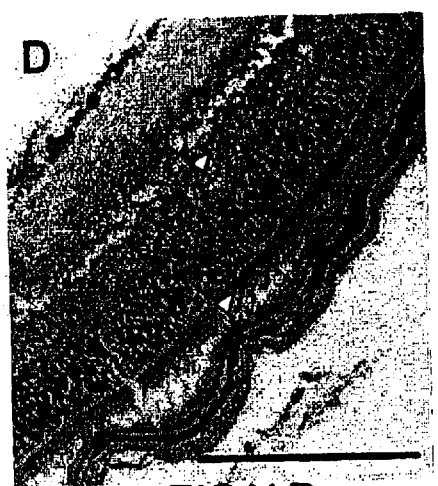
Figure 14E:
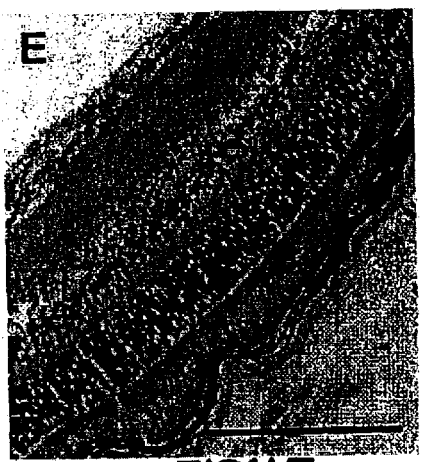
Figure 14F:
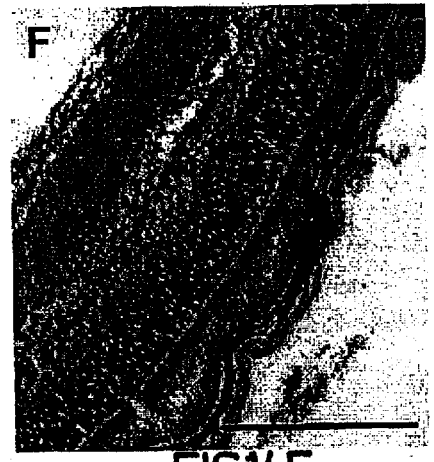

Eye Res. 65:555). To determine if PEDF is also regulated by oxygen, newborn mice were exposed to 75% oxygen (hyperoxia) from postnatal day 7 to day 12, a condition that leads to the development of undervascularized retinas (Smith, et al., 1995, Invest. Ophthalmol. Vis. Sci. 35:101) and a decline in VEGF mRNA (Pierce, et al., 1996, Arch. Ophthalmol. 114:1219). The retinas of eight of nine mice exposed to hyperoxia stained strongly for PEDF at day 12 (FIG. 14B), whereas none of 10 untreated animals remaining at normoxia (21% oxygen) showed PEDF staining (FIG. 14A). In untreated animals, levels of PEDF during retinal development followed a pattern that might be expected for an angiogenic inhibitor. PEDF immunostaining was absent or weak in three of three animals before day 18 (FIGS. 14A and 14C), when retinal vasculature is developing (Connolly, et al., 1988, Microvas. Res. 36:275), but strong in four or four mice (FIG. 14D) at day 21 and in six of six adults when neovascularization of the retina is essentially complete (Connolly, et al., 1988, Microvas. Res. 36:275). Highest PEDF levels were seen in the photoreceptor cell layer, the most avascular layer of the retina.

Figure 15A:
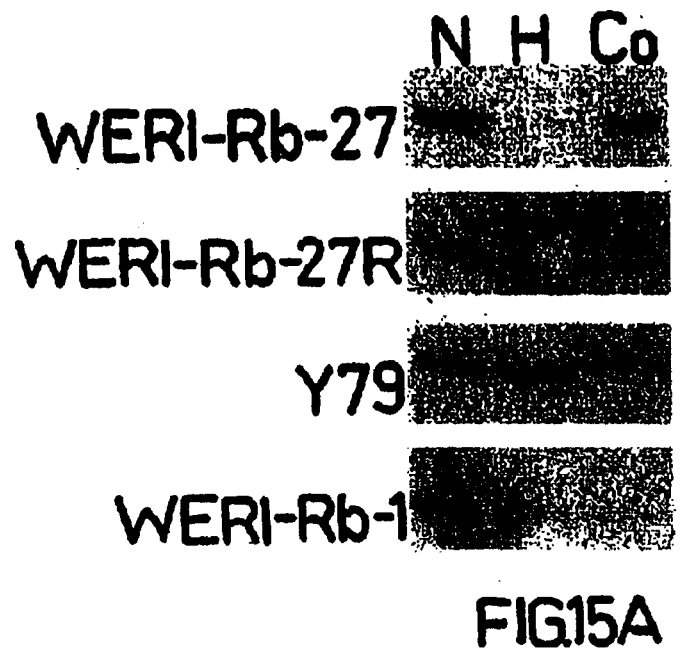
FIGS. 15A–15C, is a series of images of immunoblots and a graph depicting hypoxia-induced down-regulation of PEDF protein in cultured retinoblastoma cells.
Figure 15B:
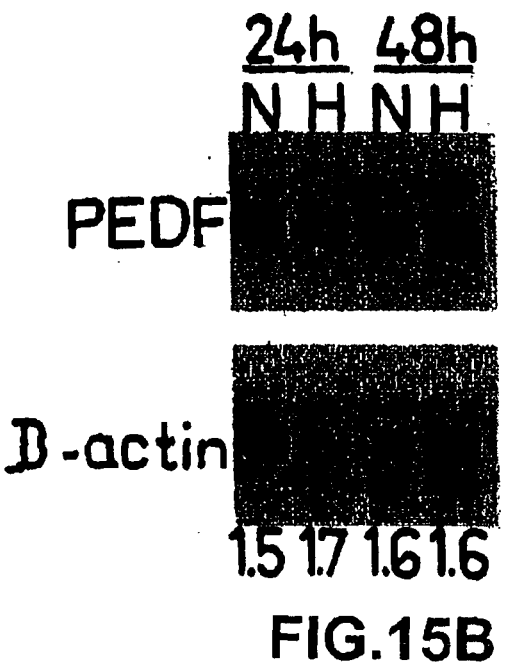

To further investigate the effect of oxygen regulation on PEDF, retinoblastoma tumor cells were maintained in low oxygen (0.5%) or in chemical agents that simulate hypoxia (Goldberg, et al., 1988, Science 242:1214). As expected, hypoxia induced a 9.5±4.8-fold rise in the level of VEGF in conditioned media as measured by enzyme-linked immunosorbent assay and reduced the level of PEDF by 11.8±4.7-fold (FIG. 15A). The responses of Rb-negative retinoblastoma cells and of revertants reexpressing Rb were similar (FIG. 15A). No difference in PEDF mRNA levels was detected among hypoxia-treated and untreated cells (FIG. 15B), suggesting that hypoxic regulation of PEDF occurred at the translational or posttranslational level.

Figure 15C:
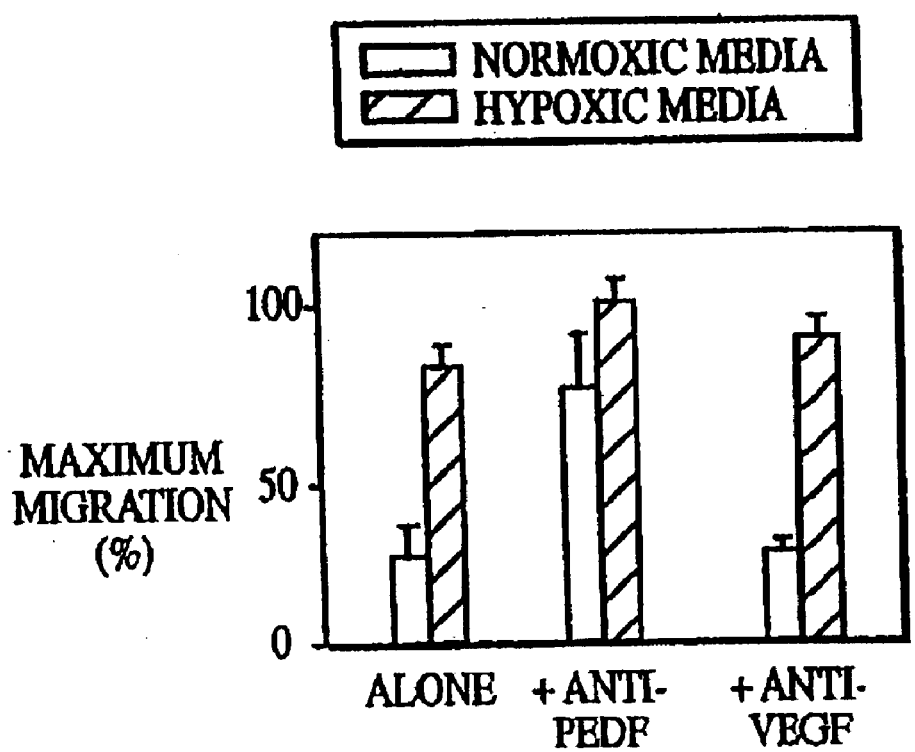

Medium conditioned by hypoxic tumor cells was more angiogenic than that conditioned by normoxic tumor cells (FIG. 15C). Hypoxia reduced the concentration of medium needed to induce 50% of maximal endothelial cell chemotaxis from 4.0 to 0.3 $\mu$g of total protein per milliliter. Neutralization of VEGF, which made only a minor contribution to the angiogenic activity of these cells, did not reduce the angiogenic activity of the hypoxic conditioned media, but neutralization of PEDF made normoxic tumor media as angiogenic as that derived from hypoxic cells. (FIG. 15C). Consistent with these in vitro studies, tumor cells present in 12 out of 12 human retinoblastoma pathologic specimens failed to stain for PEDF, presumably in part because of limited oxygen in the tumor environment (Gulledge and Dewhirst, 1996, Anticancer Res. 16:741), whereas adjacent normal retina was positive.

In summary, PEDF is likely to contribute to the regulation of blood vessel growth in the eye by creating a permissive environment for angiogenesis when oxygen is limiting (as it is in tumors and in retinopathies) and an inhibitory environment when oxygen concentrations are normal or high. Given its high potency and the broad range of angiogenic inducers against which it can act, PEDF may prove to be a useful therapeutic for pathologic ocular neovascularization as well as for retinoblastomas, where its dual activities of inducing cell differentiation (Tombran-Tink, et al., 1991, Exp. Eye Res. 53:411; Steele, et al., 1993, Proc. Natl. Acad. Sci. U.S.A. 90:1526) and inhibiting angiogenesis may be particularly effective.

Example 10

The data presented herein demonstrate amelioration of ischemic retinopathy by systemic treatment with PEDF.

Figure 16A:
FIGS. 16A–16D, is a series of images of photomicrographs depicting the effect of PEDF on retinopathy in C57/BL6 mice.
Figure 16B:
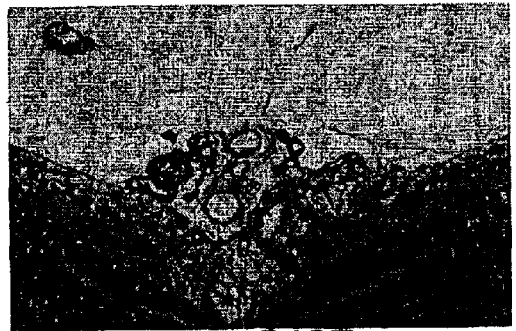
Figure 16C:
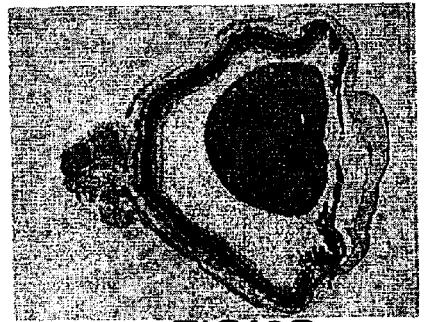
Figure 16D:
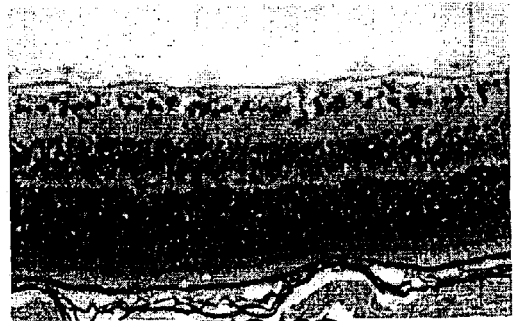
Figure 17:
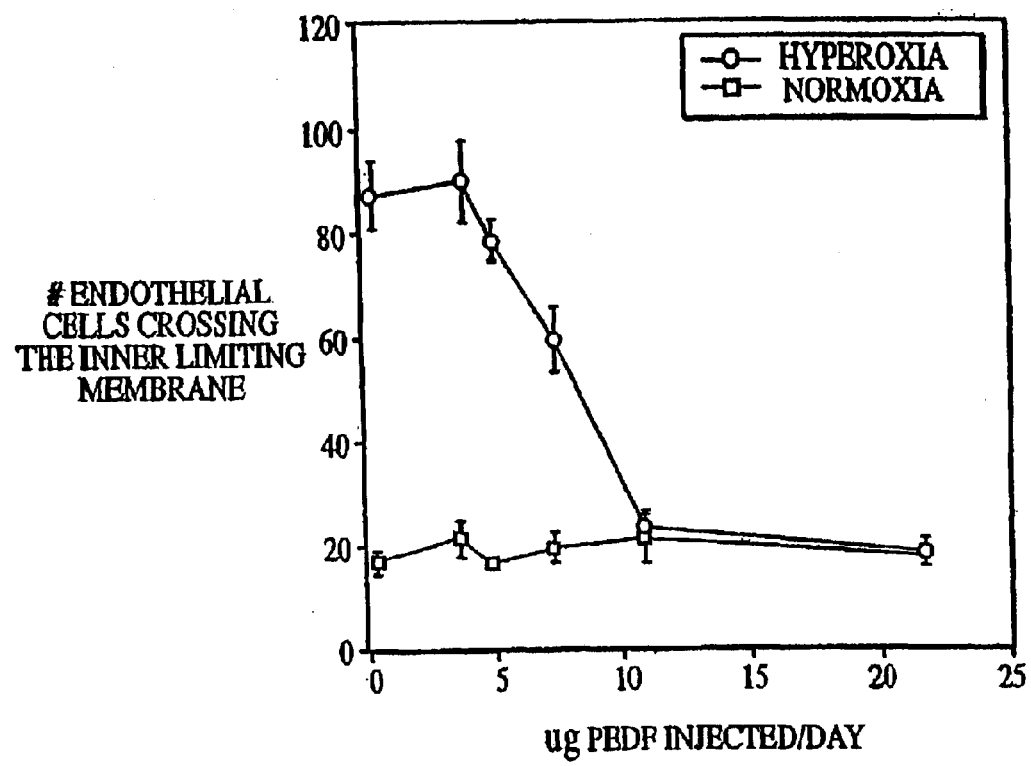
FIG. 17 is a graph depicting a dose response relationship between retinopathy and PEDF treatment in mice.

Retinopathy was induced in C57/BL6 mice by placing seven day old mice with their dams in an oxygen tent and maintaining the animals in a 75% oxygen/25% nitrogen environment until day twelve. On day twelve, the animals were removed from the tent and placed at ambient atmosphere (21% oxygen). From day twelve through day sixteen, pups were treated via intraperitoneal injection once per day with 100 $\mu$l of either phosphate buffered saline (PBS) vehicle, or 11.2 $\mu$g or 22.4 $\mu$g PEDF in PBS. Pups were anesthetized with Metaphane and perfused with 1 ml of fixative (4% paraformaldehyde/100 mM sodium phosphate buffer (pH 7.2)/4% sucrose) through the left ventricle of the heart. Eyes were removed and placed in fixative, embedded in paraffin, and processed for histologic examination. Cross sections of the eye were made, stained with hematoxylin-phloxine-saffarin (HPS), and the number of endothelial cell nuclei crossing the inner limiting membrane of the retina were counted in one cross section that contained the cornea, lens, retina and optic nerve. FIG. 16A illustrates retinopathy in the eye of a PBS treated animal, the box surrounds a vascular tuft that has penetrated the inner limiting membrane of the retinal in the low power picture. A high power view of this vascular tuft is shown in FIG. 16B. FIGS. 16C and 16D illustrate the eye of a PEDF treated mouse, no vascular tufts are present. The # of endothelial cell nuclei were quantified (Table 3). PEDF treated animals had a significant reduction in endothelial cells that had crossed the inner limiting membrane of the retina, and a dose/response relationship could be demonstrated (FIG. 17).

TABLE 3

Reduction of hyperoxia-induced ischemic retinopathy by systemic treatment with PEDF.

| Treatment | No. mice | Mean number of endothelial cell nuclei crossing ILM[a] into vitreous per cross section[b] |
|---|---|---|
| PBS vehicle | 4 | 91.3 +/− 12.0 |
| 11.2 $\mu$g PEDF/day | 5 | 18.6 +/− 2.2* |
| 22.4 $\mu$g PEDF/day | 5 | 18.2 +/− 2.5* |

*p < 0.003 compared to PBS (vehicle)
[a]ILM = inner limiting membrane
[b]Cross section of eye is in plane that includes cornea, lens, and optic nerve The disclosures of every patent, patent application, and publication cited herein are incorporated herein by reference.

While the invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method for inhibiting the growth of a tumor, said method comprising providing exogenous PEDF to endothelial cells associated with said tumor under conditions sufficient for said PEDF to inhibit the migration of said endothelial cells within and to said tumor such that the growth of said tumor is inhibited.

2. The method of claim 1, which further comprises supplying another antiangiogenic factor to said cells in conjunction with PEDF.

3. The method of claim 1, wherein said PEDF is provided to said cells by exposing a composition comprising PEDF polypeptide to said cells.

4. The method of claim 1, wherein said PEDF is supplied to said cells via the systemic circulation.

5. The method of claim 1, wherein said PEDF is supplied to said cells via topical administration.

* * * * *

SEQUENCE LISTING

<160> NUMBER OF SEQ ID NOS: 4
<210> SEQ ID NO 1
<211> LENGTH: 418
<212> TYPE: PRT
<213> ORGANISM: Homo Sapiens

<400> SEQUENCE: 1

```
Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Asp Pro Phe Phe Lys
                35                  40                  45

Val Pro Val Asn Lys Leu Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Asp Glu Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
            115                 120                 125

Val Thr Ala Pro Gln Lys Asn Leu Lys Ser Ala Ser Arg Ile Val Phe
130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
            195                 200                 205

Gly Val Ala His Phe Lys Gly Gln Trp Val Thr Lys Phe Asp Ser Arg
210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
            290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
            355                 360                 365
```

```
Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 2
<211> LENGTH: 1490
<212> TYPE: DNA
<213> ORGANISM: Homo sapiens

<400> SEQUENCE: 2
ggacgctgga ttagaaggca gcaaaaaaag atctgtgctg gctggagccc cctcagtgtg      60
caggcttaga gggactaggc tgggtgtgga gctgcagcgt atccacaggc cccaggatgc     120
aggccctggt gctactcctc tgcattggag ccctcctcgg gcacagcagc tgccagaacc     180
ctgccagccc cccggaggag ggctccccag accccgacag cacaggggcg ctggtggagg     240
aggaggatcc tttcttcaaa gtccccgtga caagctggc agcggctgtc tccaacttcg      300
gctatgacct gtaccgggtg cgatccagca tgagccccac gaccaacgtg ctcctgtctc     360
ctctcagtgt ggccacggcc ctctcggccc tctcgctggg agcggacgag cgaacagaat     420
ccatcattca ccgggctctc tactatgact tgatcagcag cccagacatc catggtacct     480
ataaggagct ccttgacacg gtcactgccc cccagaagaa cctcaagagt gcctcccgga     540
tcgtctttga gaagaagctr cgcataaaat ccagctttgt ggcacctctg aaaagtcat      600 atgggaccag gcccagagtc ctgacgggca accctcgctt ggacctgcaa gagatcaaca     660
actgggtgca ggcgcagatg aaagggaagc tcgccaggtc cacaaaggaa attcccgatg     720
agatcagcat tctccttctc ggtgtggcgc acttcaaggg gcagtgggta acaaagtttg     780
actccagaaa gacttccctc gaggatttct acttggatga agagaggacc gtgagggtcc     840
ccatgatgtc ggaccctaag gctgttttac gctatggctt ggattcagat ctcagctgca     900
agattgccca gctgccctg accggaagca tgagtatcat cttcttcctg ccctgaaag       960 tgacccagaa tttgaccttg atagaggaga gcctcacctc cgagttcatt catgacatag    1020
accgagaact gaagaccgtg caggcggtcc tcactgtccc caagctgagg ctgagttacg    1080
aaggcgaagt caccaagtcc ctgcaggaga tgaagctgca atccttgttt gattcaccag    1140
actttagcaa gatcacaggc aaacccatca agctgactca ggtggaacac cgggctggct    1200
ttgagtggaa cgaggatggg gcgggaacca ccccagccc agggctgcag cctgcccacc     1260
tcaccttccc gctggactat caccttaacc agcctttcat cttcgtactg agggacacag    1320
acacaggggc ccttctcttc attggcaaga ttctggaccc caggggcccc taatatccca    1380
gtttaatatt ccaatacccct agaagaaaac ccgagggaca gcagattcca caggacacga    1440
aggctgcccc tgtaaggttt caatgcatac aataaaagag ctttatccct                1490

<210> SEQ ID NO 3
<211> LENGTH: 21
<212> TYPE: PRT
<213> ORGANISM: Homo sapiens
<220> FEATURE:
<221> NAME/KEY: UNSURE
<222> LOCATION: (20)..(20)
<223> OTHER INFORMATION: X can be any amino acid
```

```
<400> SEQUENCE: 3

Thr Ser Leu Glu Asp Phe Tyr Leu Asp Glu Glu Arg Thr Val Arg Val
1               5                   10                  15

Pro Met Met Xaa Asp
            20

<210> SEQ ID NO 4
<211> LENGTH: 10
<212> TYPE: PRT
<213> ORGANISM: Homo sapiens
<220> FEATURE:
<221> NAME/KEY: UNSURE
<222> LOCATION: (9)..(9)
<223> OTHER INFORMATION: X can be any amino acid

<400> SEQUENCE: 4

Ile Ala Gln Leu Pro Leu Thr Gly Xaa Met
1               5                   10
```